US012169282B2

(12) United States Patent
Knoppert et al.

(10) Patent No.: US 12,169,282 B2
(45) Date of Patent: Dec. 17, 2024

(54) METHOD AND APPARATUS FOR A FRAME, SHROUD, AND FACE MASK FOR A HEAD MOUNTED DISPLAY DEVICE

(71) Applicant: Dell Products, LP, Round Rock, TX (US)

(72) Inventors: Michiel Sebastiaan Emanuel Petrus Knoppert, Amsterdam (NL); Thomas Marcus Hinskens, Utrecht (NL); Loo Shing Tan, Singapore (SG); Gerald Rene Pelissier, Mendham, NJ (US); Martin Douglas Sawtell, Singapore (SG)

(73) Assignee: DELL PRODUCTS LP, Round Rock, TX (US)

( * ) Notice: Subject to any disclaimer, the term of this patent is extended or adjusted under 35 U.S.C. 154(b) by 201 days.

(21) Appl. No.: 17/732,072

(22) Filed: Apr. 28, 2022

(65) Prior Publication Data
US 2023/0350213 A1 Nov. 2, 2023

(51) Int. Cl.
| | | |
|---|---|---|
| *G02B 27/01* | (2006.01) | |
| *A61F 9/02* | (2006.01) | |
| *D03D 1/00* | (2006.01) | |
| *G06F 1/16* | (2006.01) | |
| *G06F 3/01* | (2006.01) | |
| *D03D 11/00* | (2006.01) | |
| *D03D 13/00* | (2006.01) | |
| *D03D 17/00* | (2006.01) | |

(52) U.S. Cl.
CPC ............ *G02B 27/0176* (2013.01); *A61F 9/02* (2013.01); *G06F 1/163* (2013.01); *G06F 3/011* (2013.01); *D03D 1/00* (2013.01); *D03D 11/00* (2013.01); *D03D 13/004* (2013.01); *D03D 17/00* (2013.01); *D10B 2401/02* (2013.01); *D10B 2401/18* (2013.01); *D10B 2401/20* (2013.01)

(58) Field of Classification Search
None
See application file for complete search history.

(56) References Cited

U.S. PATENT DOCUMENTS

| | | | | |
|---|---|---|---|---|
| 2,631,287 | A * | 3/1953 | Malcom, Jr. | ............ A61F 9/025 2/9 |
| 5,654,786 | A * | 8/1997 | Bylander | ................. G02C 7/12 351/158 |
| 5,883,018 | A * | 3/1999 | Bourgois | ............. D03D 13/006 2/2.5 |

(Continued)

OTHER PUBLICATIONS

"Definition: Elastic." Oxford Languages. 2023. (Year: 2023).*
"Definition: Pliable." Oxford Languages. 2023. (Year: 2023).*

*Primary Examiner* — Grace Huang
(74) *Attorney, Agent, or Firm* — Prol Intellectual Property Law, PLLC; H. Kenneth Prol

(57) ABSTRACT

An extended reality (XR) head-mounted display (HMD) device may include a processor, a memory device, a power management unit, an HMD video display to present to a user an extended reality image of an environment, and an HMD housing fitted to be formed around a user's eyes. The HMD housing includes an HMD shield, an HMD hood comprising a fabric shroud operatively coupled to a shroud frame and a face mask operatively coupled to the shroud frame to interface with a suer's face and the HMD hood operatively coupled to the HMD shield.

20 Claims, 8 Drawing Sheets

(56) References Cited

U.S. PATENT DOCUMENTS

| | | | | |
|---|---|---|---|---|
| 5,903,395 | A * | 5/1999 | Rallison | G02B 27/0172 359/630 |
| 6,742,547 | B2 * | 6/2004 | Bryn | D03D 41/004 442/205 |
| 6,908,195 | B2 * | 6/2005 | Fuller | A61H 35/02 351/158 |
| 8,366,266 | B2 * | 2/2013 | Pulito | G02C 11/08 351/62 |
| 8,486,847 | B2 * | 7/2013 | Fan | D03D 11/00 442/205 |
| 8,605,008 | B1 * | 12/2013 | Prest | G02B 27/0176 345/7 |
| 8,810,482 | B2 * | 8/2014 | Abdollahi | G02B 27/0176 345/7 |
| 9,504,287 | B1 * | 11/2016 | Guffin, III | A61F 9/026 |
| 9,506,170 | B2 * | 11/2016 | Khokar | D04C 1/02 |
| 9,535,254 | B2 * | 1/2017 | Thomas | B29C 45/00 |
| 9,740,010 | B2 * | 8/2017 | Alhashim | G06F 3/011 |
| 10,007,116 | B2 * | 6/2018 | Drinkwater | A63F 13/00 |
| 10,209,524 | B2 * | 2/2019 | Drinkwater | G02B 27/0176 |
| 10,261,648 | B2 * | 4/2019 | Uken | B60R 1/072 |
| 10,321,751 | B1 * | 6/2019 | Magrath | G06F 1/1686 |
| 10,330,887 | B2 * | 6/2019 | Bristol | G02B 7/12 |
| 10,345,902 | B1 * | 7/2019 | Yildiz | G02B 27/0093 |
| 10,529,063 | B2 * | 1/2020 | Rodriguez | G06F 1/3265 |
| 10,764,566 | B2 * | 9/2020 | Sullivan | G06Q 20/321 |
| 10,768,441 | B2 * | 9/2020 | Kong | G02B 27/0176 |
| 10,823,971 | B2 * | 11/2020 | Maric | G02B 27/0176 |
| 10,863,637 | B1 * | 12/2020 | Pickett | H05K 5/0204 |
| 10,866,642 | B2 * | 12/2020 | Rosenberg | G06F 3/0416 |
| 10,895,890 | B2 * | 1/2021 | Lee | H04R 1/1016 |
| 11,131,856 | B2 * | 9/2021 | Gwak | G02B 27/0176 |
| 11,167,503 | B2 * | 11/2021 | Bonner | C08J 5/048 |
| 11,437,630 | B2 * | 9/2022 | Berner | H01M 8/1004 |
| 11,480,801 | B1 * | 10/2022 | Morris | A61F 9/02 |
| 11,639,567 | B2 * | 5/2023 | Lawrence | D02G 3/328 66/196 |
| 11,768,373 | B2 * | 9/2023 | Wang | G02B 27/0149 359/630 |
| 2002/0094740 | A1 * | 7/2002 | Li | D04B 1/14 442/268 |
| 2014/0224374 | A1 * | 8/2014 | Tseng | B32B 5/024 139/411 |
| 2019/0350290 | A1 * | 11/2019 | Blake | A42B 1/046 |
| 2020/0278556 | A1 * | 9/2020 | Chae | G06F 3/011 |
| 2021/0236915 | A1 * | 8/2021 | Rudell | A63F 13/323 |
| 2022/0080701 | A1 * | 3/2022 | Zulifqar | A41D 31/305 |
| 2023/0152594 | A1 * | 5/2023 | Davidson | G06F 1/203 359/601 |
| 2023/0350620 | A1 * | 11/2023 | Knoppert | G06F 3/14 |

* cited by examiner

METHOD AND APPARATUS FOR A FRAME, SHROUD, AND FACE MASK FOR A HEAD MOUNTED DISPLAY DEVICE

FIELD OF THE DISCLOSURE

The present disclosure generally relates to a head mounted display (HMD) device. The present disclosure more specifically relates to a frame, shroud, and face mask used with the HMD device.

BACKGROUND

As the value and use of information continues to increase, individuals and businesses seek additional ways to process and store information. One option available to clients is information handling systems. An information handling system generally processes, compiles, stores, and/or communicates information or data for business, personal, or other purposes thereby allowing clients to take advantage of the value of the information. Because technology and information handling needs and requirements vary between different clients or applications, information handling systems may also vary regarding what information is handled, how the information is handled, how much information is processed, stored, or communicated, and how quickly and efficiently the information may be processed, stored, or communicated. The variations in information handling systems allow for information handling systems to be general or configured for a specific client or specific use, such as e-commerce, financial transaction processing, airline reservations, enterprise data storage, or global communications. In addition, information handling systems may include a variety of hardware and software components that may be configured to process, store, and communicate information and may include one or more computer systems, data storage systems, and networking systems. The information handling system may include telecommunication, network communication, and video communication capabilities. Further, the information handling system may be operatively coupled to an extended reality (XR) device such as a head mounted display (HMD) device that allows a user to view a simulated XR environment.

BRIEF DESCRIPTION OF THE DRAWINGS

It will be appreciated that for simplicity and clarity of illustration, elements illustrated in the Figures are not necessarily drawn to scale. For example, the dimensions of some elements may be exaggerated relative to other elements. Embodiments incorporating teachings of the present disclosure are shown and described with respect to the drawings herein, in which.

The use of the same reference symbols in different drawings may indicate similar or identical items.

DETAILED DESCRIPTION OF THE DRAWINGS

Figure 1:
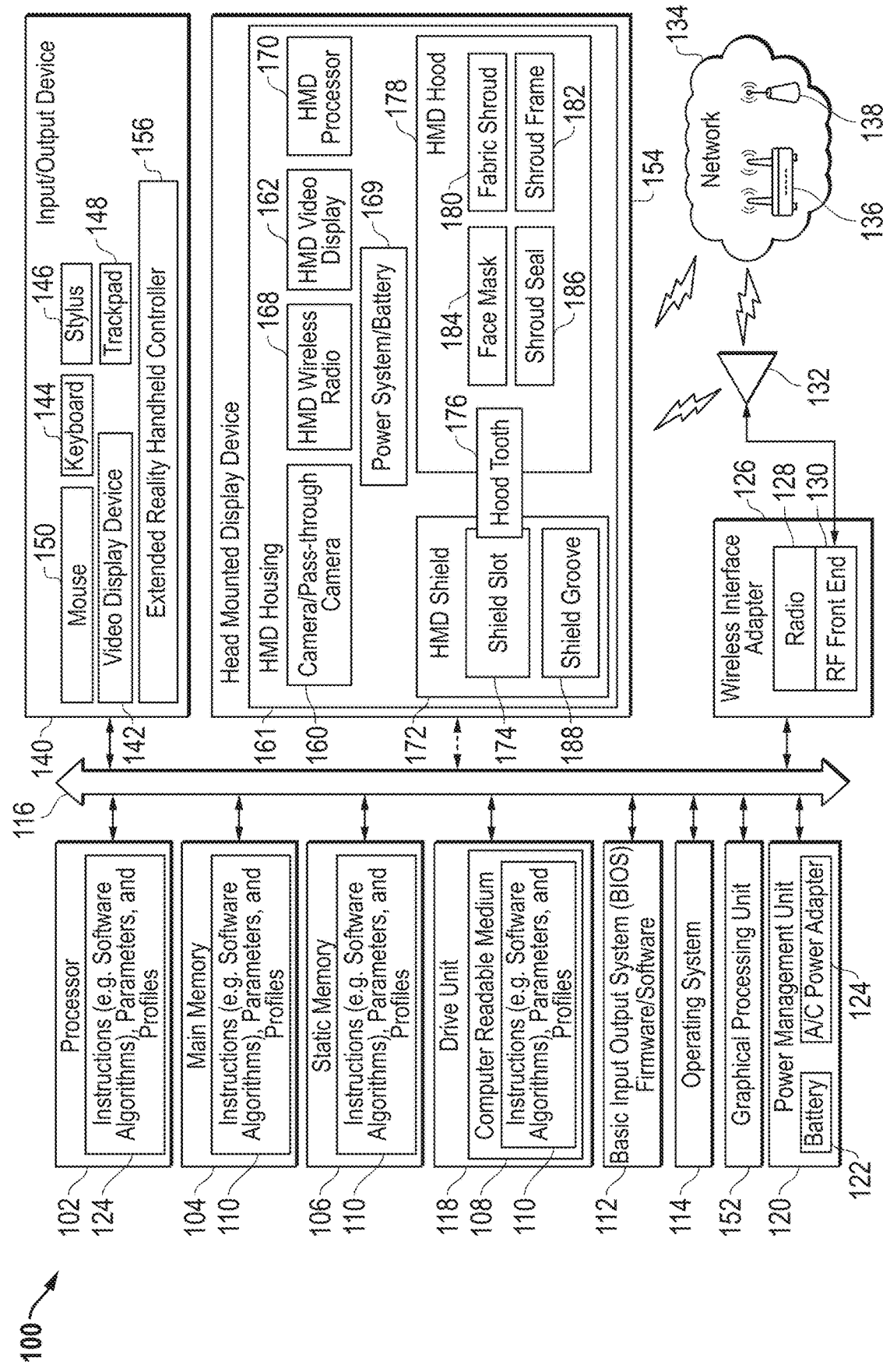
FIG. 1 is a block diagram illustrating an information handling system with a head mounted display (HMD) device having an HMD hood according to an embodiment of the present disclosure.

The following description in combination with the Figures is provided to assist in understanding the teachings disclosed herein. The description is focused on specific implementations and embodiments of the teachings and is provided to assist in describing the teachings. This focus should not be interpreted as a limitation on the scope or applicability of the teachings.

Head mounted display (HMD) devices may be wearable around the user's head and/or eyes and have the capability of providing displayed or projected images to a user. In an example, a user may be provided with a completely virtual reality (VR) environment while using the HMD device. In another example, the HMD devices may allow the user to see through those displayed or projected images in, for example, augmented reality (AR) or mixed reality (MR). Indeed, HMD devices may be capable of generating any type of extended reality (XR) environment such as AR, VR, MR, or any other type of XR environment provided by the HMD device and contemplated to exist along a reality-virtuality continuum.

HMD devices may be used for a variety of tasks and purposes. For example, HMD devices may be used to engage in video games, videoconferences, distance learning, virtual manufacturing, immersive training, and simulation, three-dimensional (3D) visualization and review, guided or remote assist applications, and other tasks or processes that can be done virtually. During these tasks, the user may use the HMD device for an extended period of time and may need to be as comfortable as possible when wearing the HMD device.

The present specification describes an XR HMD device that includes a processor, a memory device, a power management unit, an HMD video display to present to a user an extended reality image of an environment. The XR HMD device may further include an HMD housing fitted to be formed around a user's eyes, the HMD housing including an HMD shield, an HMD hood comprising a fabric shroud operatively coupled to a shroud frame, the hood operatively coupled to the HMD shield, and a face mask operatively coupled to the shroud frame.

In an embodiment, the HMD hood may be secured to the HMD shield using a hood tooth formed on the shroud frame. The hood tooth may interface with a shield slot formed in an HMD shield of the HMD device to secure the HMD hood to the HMD shield. In an embodiment, a plurality of hood teeth used may be increased to secure the HMD hood to the HMD shield at different locations on the HMD shield.

The fabric shroud may include a plurality layers in order to control the moisture within the fabric shroud as well as create a lightproof environment under the fabric shroud. In an embodiment, the fabric shroud includes a first layer including directionally-oriented moisture wicking fibers, a second layer including fibers woven in a first direction, and a third layer including fibers woven in a second direction different from the first direction to enhance light blocking of the fabric shroud. It is understood that the HMD hood is designed to restrict or limit light leaking into the HMD hood when the HMD device is worn by the user for improved viewing of XR images and XR environment in embodiments herein. For purposes herein, the prevention or limitation on light entering the HMD hood is referred to as lightproofing or making lightproof although some light may leak in in some circumstances.

The method of forming the HMD hood may include securing the fabric shroud to the shroud frame. In an embodiment, the fabric shroud may be secured to the shroud frame using, for example, a fabric to plastic welding process such as an ultrasonic or heat welding process. In another embodiment, the fabric shroud may be glued to the shroud frame. In an embodiment, the fabric shroud may be formed along a fabric shroud perimeter formed on the shroud frame. The fabric shroud extends from the proximal aperture of the shroud frame to the front, distal aperture of the shroud frame.

FIG. 1 illustrates an information handling system 100 similar to information handling systems according to several aspects of the present disclosure. In the embodiments described herein, an information handling system 100 includes any instrumentality or aggregate of instrumentalities operable to compute, classify, process, transmit, receive, retrieve, originate, switch, store, display, manifest, detect, record, reproduce, handle, or use any form of information, intelligence, or data for business, scientific, control, entertainment, or other purposes. For example, an information handling system 100 can be a personal computer, mobile device (e.g., personal digital assistant (PDA) or smart phone), server (e.g., blade server or rack server), a consumer electronic device, a network server or storage device, a network router, switch, or bridge, wireless router, or other network communication device, a network connected device (cellular telephone, tablet device, etc.), IoT computing device, wearable computing device, a set-top box (STB), a mobile information handling system, a palmtop computer, a laptop computer, a convertible laptop, a tablet, a smartphone, a desktop computer, a communications device, an access point (AP), a base station transceiver, a wireless telephone, a control system, a camera, a scanner, a printer, a personal trusted device, a web appliance, or any other suitable machine capable of executing a set of instructions (sequential or otherwise) that specify actions to be taken by that machine, and can vary in size, shape, performance, price, and functionality.

In a networked deployment, the information handling system 100 may operate in the capacity of a server or as a client computer in a server-client network environment, or as a peer computer system in a peer-to-peer (or distributed) network environment. In a particular embodiment, the computer system 100 can be implemented using electronic devices that provide voice, video, or data communication. For example, an information handling system 100 may be any mobile or other computing device capable of executing a set of instructions (sequential or otherwise) that specify actions to be taken by that machine. In an embodiment, the information handling system 100 may be operatively coupled to a server or other network device as well as with an HMD device 154 and provide data storage resources, processing resources, and/or communication resources to the HMD device 154 as described herein. Further, while a single information handling system 100 is illustrated, the term "system" shall also be taken to include any collection of systems or sub-systems that individually or jointly execute a set, or multiple sets, of instructions to perform one or more computer functions.

The information handling system 100 may include memory (volatile (e.g., random-access memory, etc.), non-volatile (read-only memory, flash memory etc.) or any combination thereof), one or more processing resources, such as a central processing unit (CPU), a graphics processing unit (GPU), processing, hardware, controller, or any combination thereof. Additional components of the information handling system 100 can include one or more storage devices, one or more communications ports for communicating with external devices, as well as various input and output (I/O) devices 140, such as a keyboard 144, a mouse 150, a video display device 142, a stylus 146, a trackpad 148, and an XR handheld controller 156, or any combination thereof. The information handling system 100 can also include one or more buses 116 operable to transmit data communications between the various hardware components described herein. Portions of an information handling system 100 may themselves be considered information handling systems and some or all of which may be wireless.

Information handling system 100 can include devices or modules that embody one or more of the devices or execute instructions for the one or more systems and modules described above and operates to perform one or more of the methods described above. The information handling system 100 may execute code instructions 110 via processing resources that may operate on servers or systems, remote data centers, or on-box in individual client information handling systems according to various embodiments herein. In some embodiments, it is understood any or all portions of code instructions 110 may operate on a plurality of information handling systems 100.

The information handling system 100 and HMD device 154 may include processing resources such as a processor 102 such as a central processing unit (CPU), accelerated processing unit (APU), a neural processing unit (NPU), a vision processing unit (VPU), an embedded controller (EC), a digital signal processor (DSP), a GPU 152, a microcontroller, or any other type of processing device that executes code instructions to perform the processes described herein. Any of the processing resources may operate to execute code that is either firmware or software code. Moreover, the information handling system 100 can include memory such as main memory 104, static memory 106, computer readable medium 108 storing instructions 110 of, in an example embodiment, an HMD application or other computer executable program code, and drive unit 118 (volatile (e.g., random-access memory, etc.), nonvolatile (read-only memory, flash memory etc.) or any combination thereof).

As shown, the information handling system 100 may further include a video display device 142. The video display device 142, in an embodiment, may function as a liquid crystal display (LCD), an organic light emitting diode (OLED), a flat panel display, or a solid-state display. Although FIG. 1 shows a single video display device 142, the present specification contemplates that multiple video display devices 142 may be used with the information handling system to facilitate an extended desktop scenario, for example. Additionally, the information handling system 100 may include one or more input/output devices 140 including an alpha numeric input device such as a keyboard 144 and/or a cursor control device, such as a mouse 150, touchpad/trackpad 148, a stylus 146, a XR handheld controller 156, or a gesture or touch screen input device associated with the video display device 142 that allow a user to interact with the images, windows, and applications presented to the user. In an embodiment, the video display device 142 may provide output to a user that includes, for example, one or more windows describing one or more instances of applications being executed by the processor 102 of the information handling system. In this example embodiment, a window, icons, or display images may be presented to the user for interaction with software applications in an XR environment. For example, a window that provides a GUI may represent the execution of a word processing application, a GUI may represent the execution of a spreadsheet application, a GUI may represent the execution of a computer-aided design application, a GUI or display images may represent the execution of a gaming application, a GUI may represent the execution of an email application, or a GUI or images may represent the execution of a web browsing application in various example embodiments. Further, an image generation application such as presentation software, or a drawing program, among others may generate other images for display. An OS may generate icons and other interactive features. In an embodiment, each of these windows, icons, or display images may be represented on the HMD video display 162 of the HMD device 154 when the HMD device 154 is being used by the user. The presentation of these windows, icons, or display images on the HMD video display 162 may be accomplished via execution of an application programming interface (API). In an embodiment, the information handling system 100 may include one or more APIs that allow the information handling system 100 to cause certain applications to be executed on the HMD device 154. These APIs may be associated with one or more sets of instructions (e.g., software algorithms), parameters, and profiles 110 that, during execution of an XR environment at the HMD device 154, causes these applications to be represented to the user within the XR environment. For example, a gaming application being executed by the processor 102 of the information handling system 100 may include an API that, when the HMD device 154 is being used by the user, allows that application to be executed at the HMD device 154 with the user being allowed to interact with the gaming application and maintain updates to changes made in the XR environment. It is appreciated that other types of applications may also be associated with APIs that allow those applications to be reproduced in an XR environment at the HMD device 154 including word processing applications, drawing applications, videoconferencing applications, among others.

In an embodiment, the information handling system 100 may be local to the user who may operate the HMD device 154. The information handling system 100 and/or HMD device 154 are operatively coupled to a network 134 via a wireless interface adapter 126 or a wireless interface adapter within the HMD device 154 via an HMD wireless radio 168, respectively. In an embodiment, the HMD device 154 and XR handheld controller 156 may be operatively coupled to one another and, optionally, to the information handling system 100 either via a wired or wireless connection such as Bluetooth or other protocol as described herein.

The network interface device of the information handling system 100 shown as wireless interface adapter 126 can provide connectivity among devices such as with Bluetooth or to a network 134, e.g., a wide area network (WAN), a local area network (LAN), wireless local area network (WLAN), a wireless personal area network (WPAN), a wireless wide area network (WWAN), or other network. In an embodiment, the WAN, WWAN, LAN, and WLAN may each include an access point 136 or base station 138 used to operatively couple the information handling system 100 and/or the HMD device 154 (e.g., via the HMD wireless radio) to a network 134. In a specific embodiment, the network 134 may include macro-cellular connections via one or more base stations 138 or a wireless access point 136 (e.g., Wi-Fi or WiGig), or such as through licensed or unlicensed WWAN small cell base stations 138. Connectivity may be via wired or wireless connection. For example, wireless network access points 136 or base stations 138 may be operatively connected to the information handling system 100 and, in an embodiment, the HMD device 154. Wireless interface adapter 126 may include one or more radio frequency (RF) subsystems (e.g., radio 128) with transmitter/receiver circuitry, modem circuitry, one or more antenna front end circuits 130, one or more wireless controller circuits, amplifiers, antennas 132 and other circuitry of the radio 128 such as one or more antenna ports used for wireless communications via multiple radio access technologies (RATs). The radio 128 may communicate with one or more wireless technology protocols. In and embodiment, the radio 128 may contain individual subscriber identity module (SIM) profiles for each technology service provider and their available protocols for any operating subscriber-based radio access technologies such as cellular LTE communications.

In an example embodiment, the wireless interface adapter 126, radio 128, and antenna 132 and HMD wireless radio 168 may provide connectivity to one or more of the peripheral devices that may include a wireless video display device 142, a wireless keyboard 144, a wireless mouse 150, a wireless headset such as the HMD device 154, a microphone, an audio headset, a wireless stylus 146, and a wireless trackpad 148, among other wireless peripheral devices used as input/output (I/O) devices 140 including any XR handheld controller 156 associated with the HMD device 154. In an embodiment, the HMD device 154 may include a wireless radio and an antenna to wirelessly couple the HMD device 154 to the information handling system 100 via the antenna 132 and radio 128. In an embodiment, the HMD device 154 may operate with Bluetooth radio protocols. In other embodiments, the HMD device 154 may operate with Wi-Fi 802.11 radio protocol, 5G NR radio protocols, or other wireless protocols. In an embodiment, an antenna controller operatively coupled to an operating system (OS) 114 may concurrently transceive data to and from various wireless devices such as the HMD device 154 or network 134 while a processing device of the HMD device 154 executes the applications being used in operation with the HMD device 154. In an embodiment, the processing device that executes the applications along with other processes associated with the operation of the HMD device 154 may be a processing device on the information handling system 100 (e.g., processor 102, GPU 152, among others described herein), at the HMD device 154 (e.g., HMD processor 170), or a combination of processors on these devices. In one embodiment, the HMD device 154 may be operatively coupled to the information handling system 100 via a wired connection to the bus 116, via, for example, a port in the information handling system 100.

The XR handheld controller 156 may be a peripheral input/output device 140 used by the user to interact with virtual images presented to the user via the HMD device 154. In an embodiment, the XR handheld controller 156 may be operatively coupled to the information handling system 100 via a wireless connection using the wireless interface adapter 126 operatively coupled to the bus 116. In this embodiment, input signals from the XR handheld controller 156 may be relayed to the processor 102, the HMD processor 170, or other processing device and used as input to manipulate an XR image presented to the user at the HMD device 154. In an embodiment, the XR handheld controller 156 may be operatively coupled to the bus 116 via a wired connection and receive this input as described. In another embodiment, the XR handheld controller 156 may be operatively coupled to the HMD device 154 via a wireless connection via operation of the HMD wireless radio 168 communicating with the radio 128 of the information handling system 100. In an example embodiment, the XR handheld controller 156 may provide input to a processing device (e.g., HMD processor 170) at the HMD device 154 to manipulate an XR image presented to the user at the HMD device 154. In another example embodiment, the XR handheld controller 156, being operatively coupled to the bus 116 or wireless interface adapter 126, may provide input to the processor 102 of the information handling system 100 to manipulate an XR image presented to the user at the HMD device 154. In one example embodiment, the GPU 152 of the information handling system 100 may be used to process and generate the graphics used to create the XR environment at the HMD device 154 as well as process those signals received by the XR handheld controller 156.

As described, the wireless interface adapter 126 and the HMD wireless radio 168 may include any number of antennas 132 which may include any number of tunable antennas for use with the system and methods disclosed herein. Although FIG. 1 shows a single antenna 132, the present specification contemplates that the number of antennas 132 may include more or less of the number of individual antennas shown in FIG. 1. Additional antenna system modification circuitry (not shown) may also be included with the wireless interface adapter 126 to implement coexistence control measures via an antenna controller in various embodiments of the present disclosure.

In some aspects of the present disclosure, the wireless interface adapter 126 may operate two or more wireless links. In an embodiment, the wireless interface adapter 126 may operate a Bluetooth wireless link using a Bluetooth wireless protocol. In an embodiment, the Bluetooth wireless protocol may operate at frequencies between 2.402 to 2.48 GHz. Other Bluetooth operating frequencies are also contemplated in the presented description. In an embodiment, a Bluetooth wireless link may be used to wirelessly couple the input/output devices operatively and wirelessly including the XR handheld controller 156, mouse 150, keyboard 144, stylus 146, trackpad 148, and/or video display device 142 to the bus 116 in order for these devices to operate wirelessly with the information handling system 100. In a further aspect, the wireless interface adapter 126 may operate the two or more wireless links with a single, shared communication frequency band such as with the 5G standard relating to unlicensed wireless spectrum for small cell 5G operation or for unlicensed Wi-Fi WLAN operation in an example aspect. For example, a 2.4 GHz/2.5 GHz or 5 GHz wireless communication frequency bands may be apportioned under the 5G standards for communication on either small cell WWAN wireless link operation or Wi-Fi WLAN operation. In some embodiments, the shared, wireless communication band may be transmitted through one or a plurality of antennas 132 may be capable of operating at a variety of frequency bands. In a specific embodiment described herein, the shared, wireless communication band may be transmitted through a plurality of antennas used to operate in an N×N MIMO array configuration where multiple antennas 132 are used to exploit multipath propagation which may be any variable N. For example, N may equal 2, 3, or 4 to be 2×2, 3×3, or 4×4 MIMO operation in some embodiments. Other communication frequency bands, channels, and transception arrangements are contemplated for use with the embodiments of the present disclosure as well and the present specification contemplates the use of a variety of communication frequency bands. As described herein, the HMD device 154 also includes an antenna system (e.g., HMD wireless radio 168) used to transceive data to and from the information handling system 100 using these wireless communication protocols described herein. Additionally, or alternatively, the HMD wireless radio 168 within the HMD device 154 may be used to communicate wirelessly with a remote server at the network 134 via an access point 136 or base station 138.

The wireless interface adapter 126 may operate in accordance with any wireless data communication standards. To communicate with a wireless local area network, standards including IEEE 802.11 WLAN standards (e.g., IEEE 802.11ax-2021 (Wi-Fi 6E, 6 GHz)), IEEE 802.15 WPAN standards, WWAN such as 3GPP or 3GPP2, Bluetooth standards, or similar wireless standards may be used. Wireless interface adapter 126 may connect to any combination of macro-cellular wireless connections including 2G, 2.5G, 3G, 4G, 5G or the like from one or more service providers. Utilization of radio frequency communication bands according to several example embodiments of the present disclosure may include bands used with the WLAN standards and WWAN carriers which may operate in both licensed and unlicensed spectrums. For example, both WLAN and WWAN may use the Unlicensed National Information Infrastructure (U-NII) band which typically operates in the ~5 MHz frequency band such as 802.11 a/h/j/n/ac/ax (e.g., center frequencies between 5.170-7.125 GHz). WLAN, for example, may operate at a 2.4 GHz band, 5 GHz band, and/or a 6 GHz band according to, for example, Wi-Fi, Wi-Fi 6, or Wi-Fi 6E standards. WWAN may operate in a number of bands, some of which are proprietary but may include a wireless communication frequency band. For example, low-band 5G may operate at frequencies similar to 4G standards at 600-850 MHz. Mid-band 5G may operate at frequencies between 2.5 and 3.7 GHz. Additionally, high-band 5G frequencies may operate at 25 to 39 GHz and even higher. In additional examples, WWAN carrier licensed bands may operate at the new radio frequency range 1 (NRFR1), NFRF2, bands, and other known bands. Each of these frequencies used to communicate over the network 134 may be based on the radio access network (RAN) standards that implement, for example, eNodeB or gNodeB hardware connected to mobile phone networks (e.g., cellular networks) used to communicate with the information handling system 100. In the example embodiment, the information handling system 100 may also include both unlicensed wireless RF communication capabilities as well as licensed wireless RF communication capabilities. For example, licensed wireless RF communication capabilities may be available via a subscriber carrier wireless service operating the cellular networks. With the licensed wireless RF communication capability, a WWAN RF front end (e.g., antenna front end 130 circuits) of the information handling system 100 may operate on a licensed WWAN wireless radio with authorization for subscriber access to a wireless service provider on a carrier licensed frequency band.

In other aspects, the information handling system 100 operating as a mobile information handling system may operate a plurality of wireless interface adapters 126 for concurrent radio operation in one or more wireless communication bands. The plurality of wireless interface adapters 126 may further share a wireless communication band or operate in nearby wireless communication bands in some embodiments. Further, harmonics and other effects may impact wireless link operation when a plurality of wireless links are operating concurrently as in some of the presently described embodiments.

The wireless interface adapter 126 can represent an add-in card, wireless network interface module that is integrated with a main board of the information handling system 100 or integrated with another wireless network interface capability, or any combination thereof. In an embodiment the wireless interface adapter 126 or an HMD wireless radio 168 may include one or more radio frequency subsystems including transmitters and wireless controllers for connecting via a multitude of wireless links. In an example embodiment, an information handling system 100 may have an antenna system transmitter for Bluetooth, 5G small cell WWAN, or Wi-Fi WLAN connectivity and one or more additional antenna system transmitters for macro-cellular communication. The RF subsystems and radios 128 and for the HMD wireless radio 168 include wireless controllers to manage authentication, connectivity, communications, power levels for transmission, buffering, error correction, baseband processing, and other functions of the wireless interface adapter 126 and for the HMD wireless radio 168.

In an embodiment, the HMD device 154 may include its own XR software platform and applications. For example, the HMD device 154 may include a game engine such as Unity (ID developed by Unity Technologies or Unreal® developed by Epic Games that may be used to help design the XR software used to operate the HMD device 154. The HMD device 154 may also include standards such as Open XR® developed by Khronos Group that allows developers to build applications that may work across a variety of HMD devices 154. Development kits such as Vuforia Nvidia Omniverse® developed by Nvidia GTC, ARCore® developed by Google, Qualcomm XR® developed by Qualcomm, may also be executed by the HMD device 154 in order to provide for the development of AR applications and markless tracking algorithms and computer code to be executed by the HMD device 154. These kits and standards, among others, may be used to develop executable program code and provide content to the user at the HMD device 154.

In an embodiment, the HMD device 154 may include its own wireless interface adapter, radio, antenna front end, and antenna such as the HMD wireless radio 168. This may allow the HMD device 154 to communicate with the information handling system 100 or, alternatively, directly to a network maintaining a remote server used to provide the XR environment to the user (e.g., software as a service, storage as a service, processing as a service). As such, this wireless interface adapter, radio, antenna front end, and antenna of the HMD wireless radio 168 may conserve processing resources of the HMD processor 170 and/or processor 102/GPU 152 of the HMD device 154 and information handling system 100 if necessary. With the wireless interface adapter, radio, antenna front end, and antenna of the HMD wireless radio 168 of the HMD device 154, the HMD device 154 may communicate with the information handling system 100 or the network 134 via an out-of-band (OOB) communication channel, for example. The OOB communication may initially facilitate the communication of the HMD device 154 with the information handling system 100 or some external sensors via, for example, Bluetooth or Wi-Fi communication protocols. In an embodiment, the OOB communication may also be accomplished using those wireless communication protocols described in connection with the operation of the wireless interface adapter 126. In an embodiment, this OOB communication may occur below the basic input/output system (BIOS) 112 or OS 114 allowing the communication to proceed in the background of other processes being executed by the processor 102 or other processing device such as the GPU 152. This allows the processing resources of the processor 102 or GPU 152 of the information handling system 100 or the processing devices of the HMD device 154 to be conserved for other processing tasks associated with the processing of XR images and data associated with the display of those images to the user via the display device of the HMD device 154.

During operation, the information handling system 100 may communicate with the HMD device 154 either via a wired connection or wirelessly as described herein. The operation of the HMD device 154 may not be dependent on the information handling system 100 being in operation, in an embodiment, and the HMD device 154 may be used by the user whether the information handling system 100 is operatively coupled to the HMD device 154 or not, in some embodiments.

In an embodiment, the HMD device 154 may include the necessary hardware used to display an XR image of a surrounding physical environment while tracking the location of the HMD device 154 (and the user) within the physical environment. This hardware used may vary depending on the type of process used to display the XR image to the user. Example processes may be grouped into two general categories: inside-out positional tracking processes and outside-in tracking processes. Although, the present specification contemplates the use of outside-in tracking processes (e.g., tracking cameras and sensors placed outside of the HMD device 154), for convenience in description, the present specification describes an HMD device 154 the operates using an inside-out process of tracking the HMD device 154. With the inside-out process of tracking the HMD device 154, the HMD device 154 includes a camera/pass-through camera 160 and other sensors used to determine the location of the HMD device 154 as it moves within an environment, in an embodiment. In an embodiment, the HMD device 154 may include positional sensors such as a global positioning system (GPS) unit, an inertial measurement unit (IMU), an e-Compass unit, and/or other positional measurement tools such as an accelerometer, a capacitive transducer, a hall effect sensor, a laser doppler vibrometer, a multi-axis displacement transducer, a potentiometer, or a confocal chromatic sensor. Other positional sensors are also contemplated, including a capacitive displacement sensor, an eddy-current sensor, an ultrasonic sensor, a grating sensor, an inductive non-contact position sensor, a linear variable differential transformer, a photodiode array, a piezo-electric transducer, a proximity sensor, a rotary encoder, a seismic displacement pick-up, and a string potentiometer, along with any other positional sensors developed in the future. The positional sensors (e.g., GPS unit, IMU, and/or eCompass unit) in an embodiment may operate to measure location coordinates (x, y, z) of the HMD device 154, as well as orientation (0), velocity, and/or acceleration. Velocity, acceleration, and trajectory of the HMD device 154 in such an embodiment may be determined by comparing a plurality of measured location coordinates and orientations taken over a known period of time, or may be measured directly by onboard positional sensor such as an accelerometer. Additionally, or alternatively, Wi-Fi triangulation or other wireless multilateration may be used that uses the characteristics of nearby Wi-Fi hotspots and other wireless access points 136 or base stations 138/nodes to discover where within an environment the HMD device 154 is located. Additionally, or alternatively, an Internet-of-Things (IoT) device may be used that include sensors that may be detectable by the HMD device 154 and provides data to the HMD device 154 that it is within a physical environment.

In an embodiment, a simultaneous localization and mapping (SLAM) engine executing a SLAM process (described herein), the IoT devices, and the Wi-Fi hotspot triangulation process may all be used as data inputs to the head mounted display CPU/GPU, the processor 102 of the information handling system 100, or other operatively coupled processing resource to better determine the initial configuration and location of the HMD device 154. In an embodiment, the OOB communication channel may help to communication wirelessly with some of these sensors when determining the location of the HMD device 154. Again, in an embodiment, the HMD device 154 may include an embedded controller that operates this OOB communication link so that this communication may be conducted below the operating system of the HMD device 154. This prevents the HMD processor 170 (e.g., a processor, GPU, CPU, or other microcontroller, etc.) from having to receive and compute this data leaving the HMD processor 170 to conduct, for example, the SLAM computations described herein.

The HMD device 154 may also be capable of capturing video or still images of its surrounding environment, which may include one or more identifiable landmarks. For example, the HMD device 154 may include one or more cameras such as the camera/pass-through camera 160. These cameras may capture two-dimensional images of the surrounding environment, which may be combined with distance measurements gathered by a plurality of, for example, IR emitters and detectors to generate a three-dimensional image of the surrounding environment. The cameras, in an embodiment, may be, for example, a stereo triangulation camera, an Infrared (IR) camera, a sheet of light triangulation camera, a structured light camera, a time-of-flight or time of arrival camera, an interferometry camera, a coded aperture camera, a RGB digital camera, an infrared digital camera, a telephoto lens digital camera, a fish-eye digital camera, a wide-angle digital camera, a close-focus digital camera, or any other type of camera. The three-dimensional image generated by a processing device (e.g., the HMD processor 170, GPU 152, or processor 102 and the like) in an embodiment may be used to determine the position and orientation of the HMD device 154 with respect to the one or more landmarks with respect to the physical surroundings as well as any virtual images in a projected XR setting on the HMD device 154.

In an embodiment, a processing device either on the HMD device 154 (e.g., HMD processor 170) itself or the processor 102 in operative communication with the HMD device 154 may process this received data from these sensors and the camera in order to facilitate the presentation of an XR image of a surrounding environment to a user via a display device on the HMD device 154 as described herein. This may be done using, for example the SLAM process. The SLAM process, in an embodiment, may be employed in order to identify the position of the headset with respect to its surrounding environment, model the surrounding environment as viewed from the perspective of the headset wearer, and render the modeled image in a three-dimensional environment matching the surrounding real-world environment. The surrounding environment may be virtual or some combination of physical and virtual for XR. It does this by a processing device (e.g., processor 102 or the HMD processor 170 of the period HMD device 154) executing computer readable program code describing an algorithm that concurrently maps a surrounding XR environment the HMD device 154 is within and detects the position of the HMD device 154 within that surrounding XR environment. IR emitters and sensors housed within or mounted on the exterior surfaces of the HMD device 154 may measure such distances in an embodiment. IR emitters and sensors may be mounted in all directions around the exterior surface of the HMD device 154, in some embodiments. In other embodiments, only portions of the exterior surfaces of the wearable headsets may have infrared emitters and sensors or cameras. For example, the HMD device 154 may emit IR light in a pattern toward the physical landmark, the HMD device 154 may emit IR light, and/or the HMD device 154 may emit IR light toward the physical landmark. The cameras mounted to the HMD device 154 may then capture an image of each of the IR lights reflecting off the surfaces of the physical landmark. If the surrounding environment further includes other ambient light sources, the cameras will also detect illumination from the physical landmark reflecting such ambient light. For example, if desk lamp and/or floor lamp are turned on, the physical landmark in an embodiment may reflect ambient light generated by the lamps.

The depth of surfaces of nearby objects may be determined by analyzing the way in which the pattern of emitted IR light is distorted as it reaches surfaces of varying distances from the headset. For example, the HMD device 154 may determine the depth of the physical landmark by analyzing the way in which the pattern of emitted IR light is distorted as it reaches the surfaces of physical landmark. Similarly, the HMD device 154 may determine the depth of the physical landmark by analyzing the way in which the pattern of emitted IR light is distorted as it reaches the surfaces of physical landmark, and the HMD device 154 may determine the depth of the physical landmark by analyzing the way in which the pattern of emitted IR light is distorted as it reaches the surfaces of physical landmark. With this data and the other data from the other sensors described herein, the processing device may execute the algorithm defining the SLAM process in order to render to a user via the display device of the HMD device 154 an XR image based on a rendered image from the model generated and referenced movement within the surrounding XR environment based on movement of the HMD device 154 relative to physical landmarks.

During operation of the information handling system 100, the user may want to interact with the applications currently being executed on the HMD video display 162 by the HMD device 154. To do so, the user may wear the HMD device 154 by aligning the HMD video display 162 with the user's eyes thereby placing an HMD housing 161 against the user's face surrounding the user's eyes. A head strap may then be secured around the back of the user's head thereby securing the HMD device 154 to the user's head. In an embodiment, the HMD housing 161 may include a face mask 184 that is a padded surface that contacts the user's face to provide additional comfort to the user.

In order to provide a more comfortable experience for the user, a weight of the HMD device 154 may be reduced, thereby limiting the weight placed on the user's face when worn. In an embodiment, various hardware may be removed from off or within the HMD device 154 such as the HMD processor 170, an HMD wireless radio 168, a power source for the HMD device 154 (e.g., a battery), and a storage device among other hardware. In an embodiment, these hardware devices may be maintained offsite from the HMD device 154 and within a compute stick operatively coupled to the HMD video display 162, the camera/pass-through camera 161, and other devices such as an IR detector/IR emitter. The compute stick may be operatively coupled to these devices using, for example, an HMD connection wire. The computer stick may include, in an example embodiment, a strap or other securing device that may be used to secure the compute stick to the user's body (e.g., a user's arm) during operation of the HMD device 154.

Additionally, in order to reduce the weight of the HMD device 154, the HMD device 154 includes an HMD hood 178 with breathable, light-weight fabric in an example embodiment. The HMD hood 178 is used to provide a darkened viewing area for better viewing results of the HMD video display 162 during presentation of an XR environment and XR images. Less ambient light improves the viewing experience for the user. Typically, HMD devices includes a large outer housing, usually made of plastic that houses the hardware of the HMD device and wraps around the sides of the user's head when worn. This extra-sized housing adds weight and bulkiness to the HMD device 154 and can contribute to fatigue to the user as the user wears the HMD device 154. The HMD hood 178 may replace the typical hard wrap-around, plastic housing of the HMD device.

In order to reduce the weight of the HMD device 154, the HMD hood 178 may include a fabric shroud 180 formed over a shroud frame 182. The shroud frame 182 may be a lightweight piece of pliable and bendable plastic that is skeletonized and includes one or more supporting members for the fabric shroud 180 to be draped over the shroud frame 182. This reduces the amount of materials used to form the HMD hood 178 as well as reduce the amount of weight of the HMD hood 178 and, accordingly, the HMD device 154. The fabric shroud 180 may be made of any material that prevents light from entering through the HMD hood 178 and into the user-viewing area within the HMD device 154 such as that area between the user's eyes and the HMD video display 162 when the HMD device 154 is being worn. In an embodiment, the fabric shroud 180 includes three layers of fabric. A first fabric shroud layer may include directionally-oriented moisture wicking fibers. During operation of the HMD device 154, a user and the HMD video display 162 may generate an amount of heat within the HMD hood 178. Along with this heat, the user may perspire or fluids in the user's eyes may evaporate into the user-viewing area. This evaporation creates microscopic droplets of sweat and other fluids that are trapped within the user-viewable area and may fog the lenses of the HMD video display 162 or be uncomfortable for a user. However, the first fabric shroud layer includes directionally-oriented moisture wicking fibers that traps these microscopic droplets of sweat and other fluids and wicking them out of and away from the user-viewing area. The directionally-orientated moisture wicking fibers may be arranged to wick the moisture to a less dense portion of the first fabric shroud layer that is away from the user-viewing area. This first fabric shroud layer may, therefore, prevent condensation from building up inside the HMD hood 178, prevent fogging of the HMD video display 162, and prevent an uncomfortable physical environment for the user.

The fabric shroud 180 may further include, in an embodiment, a second layer and a third layer each used to prevent light from entering the HMD hood 178 and into the user-viewing area. The second layer may include fibers that are woven in a first direction while the third layer includes fibers woven in a second direction that is different from the first direction. In an embodiment, the direction of the woven fibers of the second layer and the third layer may be perpendicular to each other so that light may not pass through the HMD hood 178. The tightness of the weave of the second layer and third layer may be sufficient to allow the moisture wicked away from inside the HMD hood 178 by the first fabric shroud layer to pass through the second layer and third layer.

The HMD hood 178 may further include one or more hood teeth 176 formed on the shroud frame 182 of the HMD hood 178. In an embodiment, a first hood tooth 176 may be formed on a distal top edge of the shroud frame 182. In an embodiment, a second hood tooth 176 may be formed on a distal bottom edge of the shroud frame 182. With the first hood tooth 176 on a top distal edge of the shroud frame 182 and the second hood tooth 176 at a distal bottom edge of the shroud frame 182, the shroud frame 182 may be elastically bent so that the hood teeth 176 are separated further from each other. In an embodiment, the hood teeth 176 may be placed within a shield slot 174 formed in an HMD shield 172 portion of the HMD device 154. The user may then release the shroud frame 182 allowing the hood teeth 176 to seat into their respective shield slots 174 thereby securing the HMD hood 178 to the HMD shield 172 and the other parts of the HMD device 154. This allows a user to easily swap out a first HMD hood 178 for a second HMD hood 178 for replacement of a worn or damaged HMD hood 178 or for cleaning in some embodiments. In another example embodiment, the HMD device 154 may be provided with a plurality of different sized or extra HMD hoods 178. The different sizes of HMD hoods 178 may allow a user to select, from among the plurality of HMD hoods 178, a single HMD hood 178 that is sized for the user's face the best. Additionally, each user of a plurality of users may select a specific HMD hood 178 to be used by the user throughout the lifetime of the HMD device 154. This may allow multiple users to operate the HMD device 154 using their own HMD hood 178 and any face mask 184 in some embodiments. During use, the users operating the HMD device 154 may perspire or otherwise create a situation where bacteria or viruses can be spread. In order to mitigate this transmission of bacteria or viruses, each user of the HMD device 154 may be assigned an HMD hood 178 with their own face mask 184 that the users may use with the HMD device 154. The easy removal and coupling of the HMD hood 178 to the HMD shield 172 described herein, allows for the user to easily remove their assigned HMD hood 178 after using the HMD device 154 allowing the next user to couple their assigned HMD hood 178 to the HMD shield 172 of the HMD device 154. Further, the easily installation and removal of the HMD hoods 178 enables easy cleaning or replacement of the HMD hood 178 by the user.

In an embodiment, the shroud frame 182 may further include a shroud seal 186 formed along a surface of the shroud frame 182 that abuts portions of the HMD shield 172 of the HMD device 154. The shroud seal 186 may be a portion of the shroud frame 182 that conforms to a surface of the HMD shield 172 when the HMD hood 178 is installed. In an embodiment, the HMD shield 172 includes a shield groove 188 that interfaces with the shroud seal 186 formed on the shroud frame 182 of the HMD hood 178. This interfacing between the shroud seal 186 and shield groove 188 prevents light from entering into the user-viewing area within the HMD hood 178 thereby making the HMD hood 178 lightproof.

As described herein, the HMD hood 178 may include a face mask 184 used to abut a user's face when the HMD device 154 is worn. The face mask 184 may be made of a pliable material such as a foam or silicone in order to soften the interface between the HMD device 154 and the user's face making the wearing of the HMD device 154 more comfortable to the user. In an embodiment, the shroud frame 182 may include a frame bead formed along a proximal edge of the shroud frame 182. The frame bead may interface with a bead channel formed along a length of the face mask 184 that allows the face mask 184 to be wrapped around the frame bead securing the face mask 184 to the HMD hood 178. In an embodiment, the shroud frame 182 is made of a pliable plastic that bends to conform to a user's face when the HMD device is worn by the user.

The information handling system 100 can include one or more set of instructions 110 that can be executed to cause the computer system to perform any one or more of the methods or computer-based functions disclosed herein. For example, instructions 110 may execute an XR application, APIs, various software applications, software agents, or other aspects or components. Various software modules comprising application instructions 110 may be coordinated by an operating system (OS) 114, and/or via an application programming interface (API). An example OS 114 may include Windows®, Android®, and other OS types known in the art. Example APIs may include Win 32, Core Java API, or Android APIs.

The disk drive unit 118 and may include a computer-readable medium 108 in which one or more sets of instructions 110 such as software can be embedded to be executed by the processor 102 or other processing devices such as a GPU 152 to perform the processes described herein. Similarly, main memory 104 and static memory 106 may also contain a computer-readable medium for storage of one or more sets of instructions, parameters, or profiles 110 described herein. The disk drive unit 118 or static memory 106 also contain space for data storage. Further, the instructions 110 may embody one or more of the methods as described herein. In a particular embodiment, the instructions, parameters, and profiles 110 may reside completely, or at least partially, within the main memory 104, the static memory 106, and/or within the disk drive 116 during execution by the processor 102 or GPU 152 of information handling system 100. The main memory 104, GPU 152, and the processor 102 also may include computer-readable media.

Main memory 104 or other memory of the embodiments described herein may contain computer-readable medium (not shown), such as RAM in an example embodiment. An example of main memory 104 includes random access memory (RAM) such as static RAM (SRAM), dynamic RAM (DRAM), non-volatile RAM (NV-RAM), or the like, read only memory (ROM), another type of memory, or a combination thereof. Static memory 106 may contain computer-readable medium (not shown), such as NOR or NAND flash memory in some example embodiments. The applications and associated APIs described herein, for example, may be stored in static memory 106 or on the drive unit 118 that may include access to a computer-readable medium 108 such as a magnetic disk or flash memory in an example embodiment. While the computer-readable medium is shown to be a single medium, the term "computer-readable medium" includes a single medium or multiple media, such as a centralized or distributed database, and/or associated caches and servers that store one or more sets of instructions. The term "computer-readable medium" shall also include any medium that is capable of storing, encoding, or carrying a set of instructions for execution by a processor or that cause a computer system to perform any one or more of the methods or operations disclosed herein.

In ab embodiment, the information handling system 100 may further include a power management unit (PMU) 120 (a.k.a. a power supply unit (PSU)). The PMU 120 may manage the power provided to the components of the information handling system 100 such as the processor 102, a cooling system, one or more drive units 118, the GPU 152, a video/graphic display device 142 or other input/output devices 140 such as the stylus 146, a mouse 150, a keyboard 144, and a trackpad 148 and other components that may require power when a power button has been actuated by a user. In an embodiment, the PMU 120 may monitor power levels and be electrically coupled, either wired or wirelessly, to the information handling system 100 to provide this power and coupled to bus 116 to provide or receive data or instructions. The PMU 120 may regulate power from a power source such as a battery 122 or A/C power adapter 124. In an embodiment, the battery 122 may be charged via the A/C power adapter 124 and provide power to the components of the information handling system 100 via a wired connections as applicable, or when A/C power from the A/C power adapter 124 is removed. A similar HMD power system 169 with a PMU, battery, A/C adapter and other features may be provided to power the HMD device 154 and components therein.

In a particular non-limiting, exemplary embodiment, the computer-readable medium can include a solid-state memory such as a memory card or other package that houses one or more non-volatile read-only memories. Further, the computer-readable medium can be a random-access memory or other volatile re-writable memory. Additionally, the computer-readable medium can include a magneto-optical or optical medium, such as a disk or tapes or other storage device to store information received via carrier wave signals such as a signal communicated over a transmission medium. Furthermore, a computer readable medium can store information received from distributed network resources such as from a cloud-based environment. A digital file attachment to an e-mail or other self-contained information archive or set of archives may be considered a distribution medium that is equivalent to a tangible storage medium. Accordingly, the disclosure is considered to include any one or more of a computer-readable medium or a distribution medium and other equivalents and successor media, in which data or instructions may be stored.

In other embodiments, dedicated hardware implementations such as application specific integrated circuits (ASICs), programmable logic arrays and other hardware devices can be constructed to implement one or more of the methods described herein. Applications that may include the apparatus and systems of various embodiments can broadly include a variety of electronic and computer systems. One or more embodiments described herein may implement functions using two or more specific interconnected hardware modules or devices with related control and data signals that can be communicated between and through the modules, or as portions of an application-specific integrated circuit. Accordingly, the present system encompasses software, firmware, and hardware implementations.

When referred to as a "system", a "device," a "module," a "controller," or the like, the embodiments described herein can be configured as hardware. For example, a portion of an information handling system device may be hardware such as, for example, an integrated circuit (such as an Application Specific Integrated Circuit (ASIC), a Field Programmable Gate Array (FPGA), a structured ASIC, or a device embedded on a larger chip), a card (such as a Peripheral Component Interface (PCI) card, a PCI-express card, a Personal Computer Memory Card International Association (PCMCIA) card, or other such expansion card), or a system (such as a motherboard, a system-on-a-chip (SoC), or a stand-alone device). The system, device, controller, or module can include software, including firmware embedded at a device, such as an Intel® Core class processor, ARM® brand processors, Qualcomm® Snapdragon processors, or other processors and chipsets, or other such device, or software capable of operating a relevant environment of the information handling system. The system, device, controller, or module can also include a combination of the foregoing examples of hardware or software. Note that an information handling system can include an integrated circuit or a board-level product having portions thereof that can also be any combination of hardware and software. Devices, modules, resources, controllers, or programs that are in communication with one another need not be in continuous communication with each other, unless expressly specified otherwise. In addition, devices, modules, resources, controllers, or programs that are in communication with one another can communicate directly or indirectly through one or more intermediaries.

Figure 2:
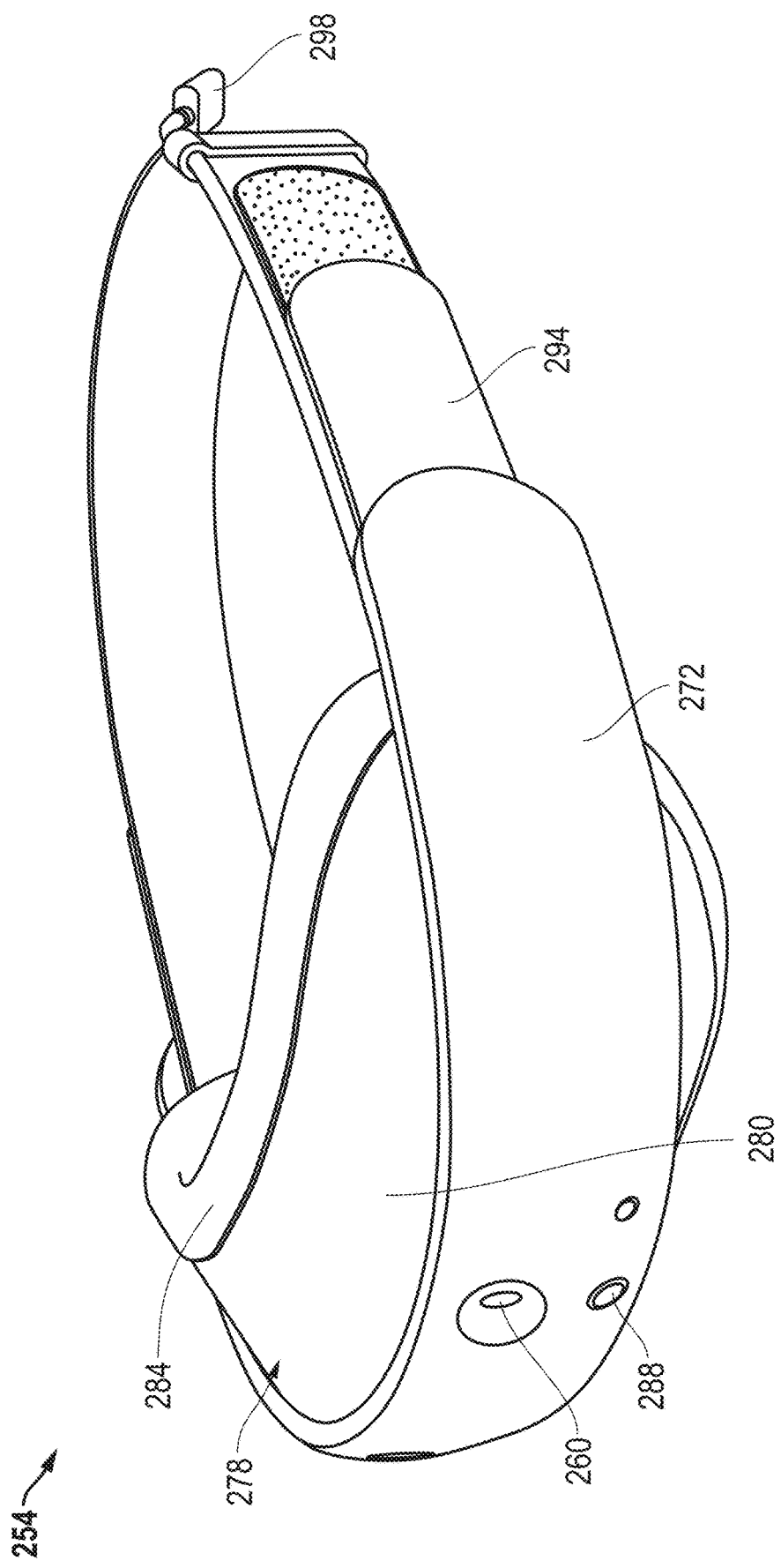
FIG. 2 is a graphic diagram perspective view of an HMD device according to an embodiment of the present disclosure.

FIG. 2 is a graphic diagram perspective view of an HMD device 254 according to an embodiment of the present disclosure. The general shape and form of the HMD device 254, in an embodiment, may be similar to a pair of wrap-around goggles. In an embodiment, the HMD device 254 may be as lightweight as possible in order to place the least amount of weight on the user's face and head during use. As such, the HMD device 254 may include an HMD connection wire 298 used to operatively couple the HMD device 254 to a processing and storage resource. In an embodiment, this processing and storage resource may be an information handling system similar to the information handling system described in connection with FIG. 1. In another embodiment, this processing and data storage resource may be a compute stick or compute compartment that includes the hardware such as a GPU/video processor, a data storage device, a power system/battery 169, a power source (e.g., the battery) among other hardware that may be operatively coupled to the HMD device 254 and HMD video display (e.g., 162, FIG. 1) but could be placed offsite from the HMD device 254 or on the back or side of the head strap 294 in order to reduce the weight of the HMD device 254 on the user's face or head. This compute stick, in an embodiment, may include a strap or other securing device that allows the user to secure the compute stick to the user's body (e.g., an arm) when operating the HMD device 254. In an embodiment, this offsite compute stick or head strap compute compartment may be operatively coupled to the HMD video display (e.g., 162, FIG. 1, not shown in FIG. 2) of the HMD device 254 in order to provide video/image data to the user during use.

The HMD device 254 may include an HMD shield 272 in an embodiment. The HMD shield 272 may act as part of the housing on to which other components of the HMD device 254 may be secured or into which some of the hardware of the HMD device 254 may be placed such as the HMD hood 278. For example, the HMD device 254 may include a camera/pass-through camera 260 used to provide data to a processing resource describing the location of the HMD device 254 within a physical environment. Additionally, the camera/pass-through camera 260 may provide images to the user via the HMD video display of the physical environment around the user. The camera/pass-through camera 260 may be formed into a front portion of the HMD shield 272 and protected from the rigid housing of the HMD shield 272 from damage.

The HMD shield 272 may also house an IR detector/IR emitter 288. In an embodiment, the IR detector/IR emitter 288 or visible light versions of the same, for example, within either on the HMD device 254 (e.g., inward-out location detection) or located within the physical environment (e.g., outward-in location detection), may be used to triangulate or multilaterate the location of the HMD device 254 within the physical environment relative to beacons or reflection of light from landmarks in the physical environment. In the example embodiment shown in FIG. 2, the IR detector/IR emitter 288 may also be placed within the housing of the HMD shield 272 to protect the IR detector/IR emitter 288 from damage. Again, the data obtained from the IR detector/IR emitter 288 may be used by a SLAM engine executed by the processing resources described herein. The SLAM engine, in an embodiment, may access the position/orientation information for the one or more landmarks with respect to the HMD device 254 generated or received by the HMD CPU/GPU/XR processor, the data from the IR detector/IR emitter 288, and other orientation data described herein, and use this information to generate a three-dimensional virtual map of HMD device 254 and its surrounding environment, including the one or more identified landmarks. In other example embodiments, the HMD CPU/GPU/XR processor may receive one or more SLAM frames including three-dimensional virtual maps of the HMD device 254 and its surrounding environment from the remotely located laptop or desktop information handling system via a network adapter.

The HMD shield 272 may also include an HMD hood 278 operatively coupled to the HMD shield 272. Again, because the area between the user's eyes and the HMD video display needs to be dark (e.g., the user-viewing area), the HMD hood 278 may prevent light from entering this area. In an embodiment, the HMD hood 278 may be lightproof so that the user may view the images and videos presented to the user at the HMD video display. In an embodiment, the HMD hood 278 may include a shroud frame (not shown) that maintains a shape of the fabric shroud 280 of the HMD hood 278 around the user's eyes and away from the HMD video display. In an embodiment, the frame and HMD hood 278 may include a face mask 284 used to abut a user's face when the HMD device 254 is worn. The face mask 284 may be made of a pliable material such as a foam or silicone in order to soften the interface between the HMD device 254 and the user's face making the wearing of the HMD device 254 more comfortable to the user.

The HMD device 254 may further include a head strap 294. In an embodiment, the head strap 294 may be operatively coupled to the HMD shield 272 and extend away from the HMD shield 272. The head strap 294 may be sized to fit around the back a user's head and is used to secure the HMD device 254 to the user's head and face. In an embodiment, the head strap 294 may include adjustable straps such as with velcro or other fasteners that allow the user to loosen or tighten the head strap 294 around the user's head. In an embodiment, the head strap 294 may be made of an elastic material that may stretch around the user's head when the HMD device 254 is being worn.

Figure 3:
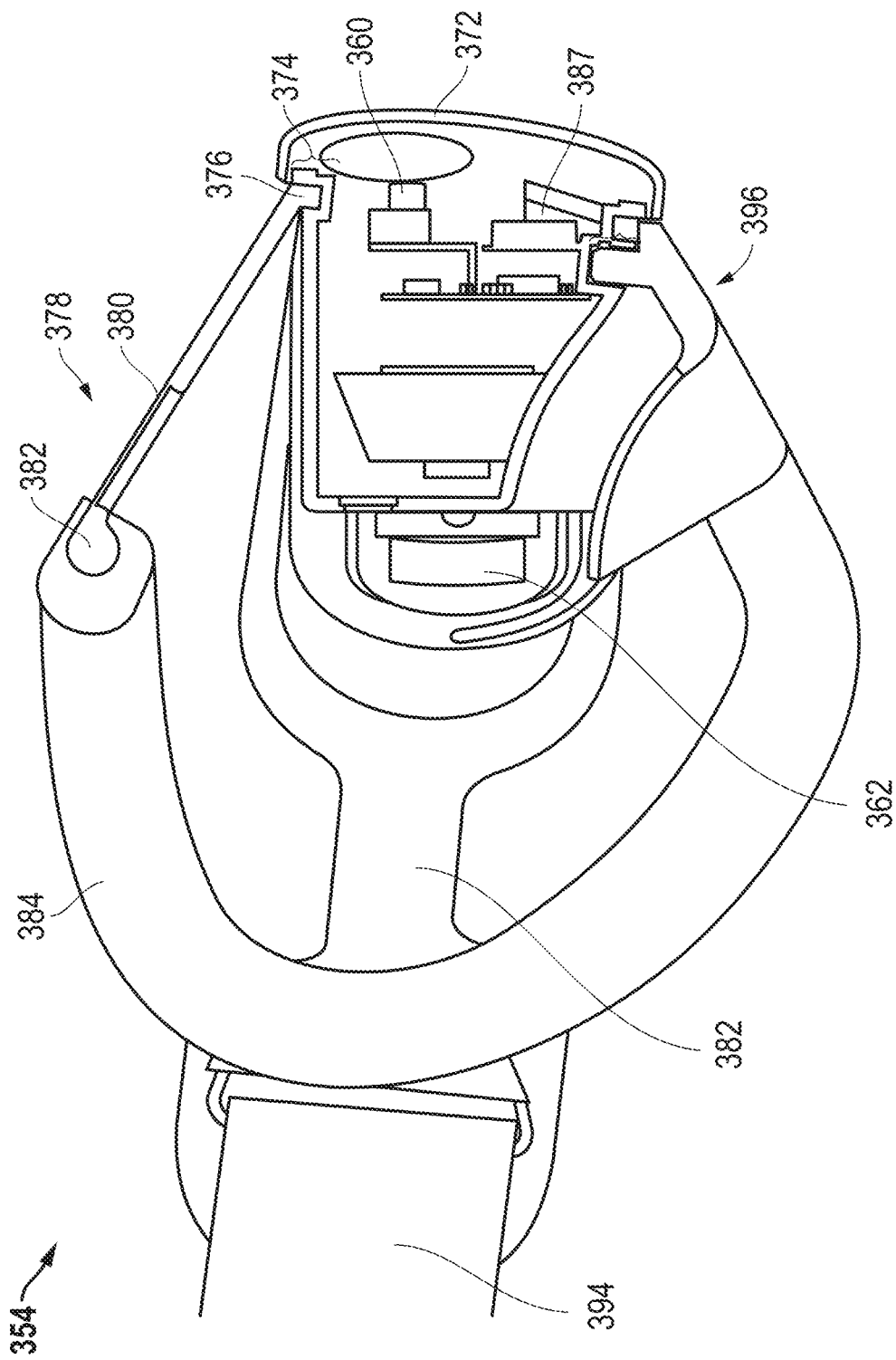
FIG. 3 is a graphic diagram side, sectional view of an HMD device and with an HMD hood according to an embodiment of the present disclosure.

FIG. 3 is a graphic diagram side, sectional view of an HMD device 354 and with an HMD hood 378 according to an embodiment of the present disclosure. This side, sectional view shows an interior portion of the HMD device 354. As described herein, the HMD device 354 includes the HMD hood 378 operatively coupled to the HMD shield 372 of the HMD device 354. Again, because the area between the user's eyes and the HMD video display 362 needs to be dark, the HMD hood 378 may prevent light from entering this area. In an embodiment, the HMD hood 378 may be lightproof so that the user may view the images and videos presented to the user at the HMD video display 362. In an embodiment, the HMD hood 378 may include a shroud frame 382 that maintains a shape of a fabric shroud 380 around the user's eyes and away from the HMD video display 362. In an embodiment, the shroud frame 382 of the HMD hood 378 may include a face mask 384 used to abut a user's face when the HMD device 354 is worn. The face mask 384 may be made of a pliable material such as a foam or silicone in order to soften the interface between the HMD device 354 and the user's face making the wearing of the HMD device 354 more comfortable to the user.

The HMD device 354 may further include a head strap 394. In an embodiment, the head strap 394 may be operatively coupled to the HMD shield 372 and extend away from the HMD shield 372. The head strap 394 may be sized to fit around the back a user's head and is used to secure the HMD device 354 to the user's head and face. In an embodiment, the head strap 394 may include adjustable straps with velcro or other fastener structures that allow the user to loosen or tighten the head strap 394 around the user's head. In an embodiment, the head strap 394 may be made of an elastic material that may stretch around the user's head when the HMD device 354 is being worn.

The HMD device 354 may include an HMD shield 372 in an embodiment. The HMD shield 372 may act as part of the housing on to which other components of the HMD device 354 may be secured or into which some of the hardware of the HMD device 354 may be placed. For example, the HMD device 354 may include a camera/pass-through camera 360 used to provide data to a processing resource describing the location of the HMD device 354 within a physical environment. Additionally, the camera/pass-through camera 360 may provide images to the user via the HMD video display 362 of the physical environment around the user. The camera/pass-through camera 360 may be formed into a front portion of the HMD shield 372 and protected from the rigid housing of the HMD shield 372 from damage.

The HMD shield 372 may also house an IR detector/IR emitter 387. In an embodiment, the IR detector/IR emitter 387 or visible light versions of the same, for example, within either on the HMD device 354 (e.g., inward-out location detection) or located within the physical environment (e.g., outward-in location detection), may be used to triangulate or multilaterate the location of the HMD device 354 within the physical environment. In the example embodiment shown in FIG. 3, the IR detector/IR emitter 387 may also be placed within the housing of the HMD shield 392 to protect the IR detector/IR emitter 387 from damage. Again, the data obtained from the IR detector/IR emitter 387 may be used by a SLAM engine executed by the processing resources described herein. The SLAM engine, in an embodiment, may access the position/orientation information for the one or more landmarks with respect to the HMD device 354 generated or received by the HMD CPU/GPU/XR processor, the data from the IR detector/IR emitter 387, and other orientation data described herein, and use this information to generate a three-dimensional virtual map of HMD device 354 and its surrounding environment, including the one or more identified landmarks. In other example embodiments, the HMD CPU/GPU/XR processor may receive one or more SLAM frames including three-dimensional virtual maps of the HMD device 354 and its surrounding environment from the remotely located laptop or desktop information handling system via a network adapter.

As described herein, the HMD device 354 includes a nose bridge 396 which may be a swappable nose bridge in some embodiments. In order to also make the user more comfortable, the HMD device 354 may include this swappable nose bridge 396. In one embodiment, the swappable nose bridge 396 may be a removable part of the HMD housing such as the HMD shield 392 that contacts the user's nose when the HMD device 354 is placed on the user's head. In another embodiment, the swappable nose bridge 396 may be one of a plurality of swappable nose bridges 396 available to the user to operatively couple to the HMD shield 392. These plurality of swappable nose bridges 396 may be of different sizes or colors to accommodate the user or a plurality of user's when interfacing with the HMD device 354. For example, a first user may have a relatively smaller nose than a second user and the plurality of swappable nose bridges 396 may be differentiated by different sizes to accommodate these differences is physiology between, in this example, the first user and the second user. In an embodiment, the plurality of swappable nose bridges 396 may be of different colors or may include other differentiating features (e.g., symbols) that allow a user to know which of the plurality of swappable nose bridges 396 belongs to that user. Using the HMD device 354 may cause different bacteria or viruses to be transmitted from one user to another. In order to mitigate this, each user may use their own swappable nose bridge 396 that is differentiated by color, for example, in order to the user to readily swap in their assigned or owned swappable nose bridge 396 to use with the HMD device 354. In an embodiment, the nose bridge or swappable nose bridge 396 may be operatively coupled into a bottom side of the HMD shield 372 at a nose bridge slot or other coupling location.

The HMD hood 378 may include a fabric shroud 380 laid over a shroud frame 382 and operatively coupled to the HMD shield 372 via and interaction between one or more shield slots 374 and one or more hood teeth 376 formed at a front edge of the shroud frame 382 along a front aperture where the HMD shield 372 is to be inserted in an embodiment. In one embodiment, the deformation of the shroud frame 382 may cause the hood teeth 376 to seat into the shield slots 374 when the shroud frame 382 aligns the hood teeth 376 with the shield slots 374 and reforms to its original shape. The interaction may be an interference or snap-fit interaction to attach the hood teeth 376 in the shield slot 374 in another embodiment. In other embodiments, fasteners, clips, or other structures may be used to secure the fabric shroud 380 to the HMD shield 372. The hood teeth 376 and shield slot 374 can be of any length, shape, or size but are complementary to engage with one another by being seated together or in an interference or snap fit in various embodiments. In an embodiment, the HMD hood 378 may include a hood edge seal interface portion or lip to fit into a groove in the HMD shield 372 that is around some or all of the HMD shield 372 in an embodiment. The hood edge seal interface or lip would correspondingly run around the edge of the shroud frame 382. The shroud frame 382 may be a lightweight piece of pliable plastic that is bendable and skeletonized and includes one or more supporting members for the fabric shroud 380 to be draped over the shroud frame 382. As shown in FIG. 3, the shroud frame 382 may include a distal edge that abuts the HMD shield 372 and a proximal edge that interfaces with a face mask 384 used to abut a user's face. FIG. 3 shows other supports members between the distal edge and proximal edge that create support between these edges on the shroud frame 382. With this skeletonized structure of the shroud frame 382, the amount of materials used to form the HMD hood 378 thereby reducing the weight of the HMD hood 378 and, accordingly, the overall weight of the HMD device 354. The fabric shroud 380 may be made of any material that prevents light from entering through the HMD hood 378 and into the user-viewing area within the HMD device 354 such as that area between the user's eyes and the HMD video display 362 when the HMD device 354 is being worn.

In an embodiment, the fabric shroud 380 includes three layers of fabric. A first fabric shroud layer may include directionally-oriented moisture wicking fibers. During operation of the HMD device 354, a user and the HMD video display 362 may generate an amount of heat within the HMD hood 378. Along with this heat, the user may perspire or fluids in the user's eyes may evaporate into the user-viewing area. This evaporation creates microscopic droplets of sweat and other fluids that are trapped within the user-viewable area. However, the first fabric shroud layer includes directionally-oriented moisture wicking fibers that traps these microscopic droplets of sweat and other fluids and wicking them out of and away from the user-viewing area. The directionally-orientated moisture wicking fibers may be arranged to wick the moisture to a less dense portion of the first fabric shroud layer that is away from the user-viewing area. This first fabric shroud layer may, therefore, prevent condensation from building up inside the HMD hood 378, over the HMD video display 362, and creating an uncomfortable physical environment for the user.

The fabric shroud 380 may further include, in an embodiment, a second layer and a third layer each used to prevent light from entering the HMD hood 378 and into the user-viewing area. The second layer may include fibers that are woven in a first direction while the third layer includes fibers woven in a second direction that is different from the first direction. In an embodiment, the direction of the woven fibers of the second layer and the third layer may be perpendicular to each other so that light may not pass through the HMD hood 378. The tightness of the weave of the second layer and third layer may be sufficient however to allow the moisture wicked away from inside the HMD hood 378 by the first fabric shroud layer to pass through the second layer and third layer in an embodiment.

The HMD hood 378 may further include one or more hood teeth 376 formed on the shroud frame 382 of the HMD hood 378 around a front aperture. FIG. 3 shows a single hood tooth 376 formed at a top, first edge around the front aperture of the HMD hood 378 while other hood teeth 376, although not shown, may be formed at a bottom, front edge of the shroud frame 382. With a first hood tooth 376 on a top, first edge of the shroud frame 382 and a second or additional hood teeth 376 formed at a first, bottom edge of the shroud frame 382, the shroud frame 382 may be elastically bent so that the hood teeth 376 are separated further from each other than what is shown in FIG. 3 to install or remove from a receiving shield slot or slots 374. This separation of the hood teeth 376 away from each other may facilitate the user in installing or removing the HMD hood 378 with or from the HMD shield 372 respectively by sliding the HMD shield 372 and housing into the front aperture of the HMD hood 378.

In an embodiment, the hood teeth 376 may be placed within a shield slot 374 formed in an HMD shield 372 portion of the HMD device 354 while installed or being installed by the user. When being installed and when the user releases the force used to bend the shroud frame 382 and to separate the hood teeth 376 from each other, the hood teeth 376 are allowed to be seated into their respective shield slots 374. In one embodiment, an interference fit or snap fit between the hood teeth 376 and shield slot 374 may be used thereby securing the HMD hood 378 to the HMD shield 372 and the other parts of the HMD device 354. Either embodiment allows a user to easily swap out a first HMD hood 378 for a second HMD hood 378. This allows for easy removal of the HMD hood for cleaning or replacement by the user in one example embodiment. In another example embodiment, the HMD device 354 may be provided with a plurality of different sized or extra HMD hoods 378. The different sizes of HMD hoods 378 may allow a user to select, from among the plurality of HMD hoods 378, a single HMD hood 378 that is sized for the user's face the best. Additionally, the user may select a specific HMD hood 378 to be used by a particular user among a plurality of users of the HMD device 354 throughout the lifetime of the HMD device 354. This may allow multiple users to operate the HMD device 354 using their own HMD hood 378 with their own HMD hood 378. During use, the users operating the HMD device 354 may perspire or otherwise create a situation where bacteria or viruses can be spread. In order to mitigate this transmission of bacteria or viruses, each user of the HMD device 354 may be assigned an HMD hood 378 that the user may use with the HMD device 354. In an embodiment, the user may be allowed to purchase additional HMD hoods 378 for this purpose or to replace worn or damaged HMD hoods 378. In one embodiment, the HMD device 354 may be shipped to the user with a plurality of HMD hoods 378 as described herein. With the easy removal and coupling of the HMD hood 378 to the HMD shield 372 as described herein, the user is allowed to easily remove their assigned HMD hood 378 after using the HMD device 354 allowing the next user to couple their assigned HMD hood 378 to the HMD shield 372 of the HMD device 354.

In an embodiment, the shroud frame 382 may further include a shroud seal (not shown) formed along a distal edge surface of the shroud frame 382 that abuts portions of the HMD shield 372 of the HMD device 354. The shroud seal may be a portion of the shroud frame 382 that conforms to a surface of the HMD shield 372 when the HMD hood 378 is installed. In an embodiment, the HMD shield 372 includes a shield groove (not shown) that interfaces with the shroud seal such as an HMD shield-side edge lip formed on the shroud frame 382 of the HMD hood 378. This interfacing between the shroud seal such as an HMD shield-side edge lip and shield groove prevents light from entering the user-viewing area within the HMD hood 378 thereby making the HMD hood 378 lightproof.

As described herein, the HMD hood 378 may include a face mask 384 used to abut a user's face when the HMD device 354 is worn. The face mask 384 may be made of a pliable material such as a foam or silicone in order to soften the interface between the HMD device 354 and the user's face making the wearing of the HMD device 354 more comfortable to the user. In an embodiment, the shroud frame 382 may include a frame bead formed along a proximal edge of the shroud frame 382, or the edge closer to the user's face.

The frame bead may interface with a bead channel formed along a length of the face mask 384 that allows the face mask 384 to be wrapped around the frame bead securing the face mask 384 to the HMD hood 378. The face mask frame bead or frame lip around a back aperture on the face side of the shroud frame 382 may also reduce or prevent external light from leaking into the HMD device 354 in some embodiments.

Figure 4:
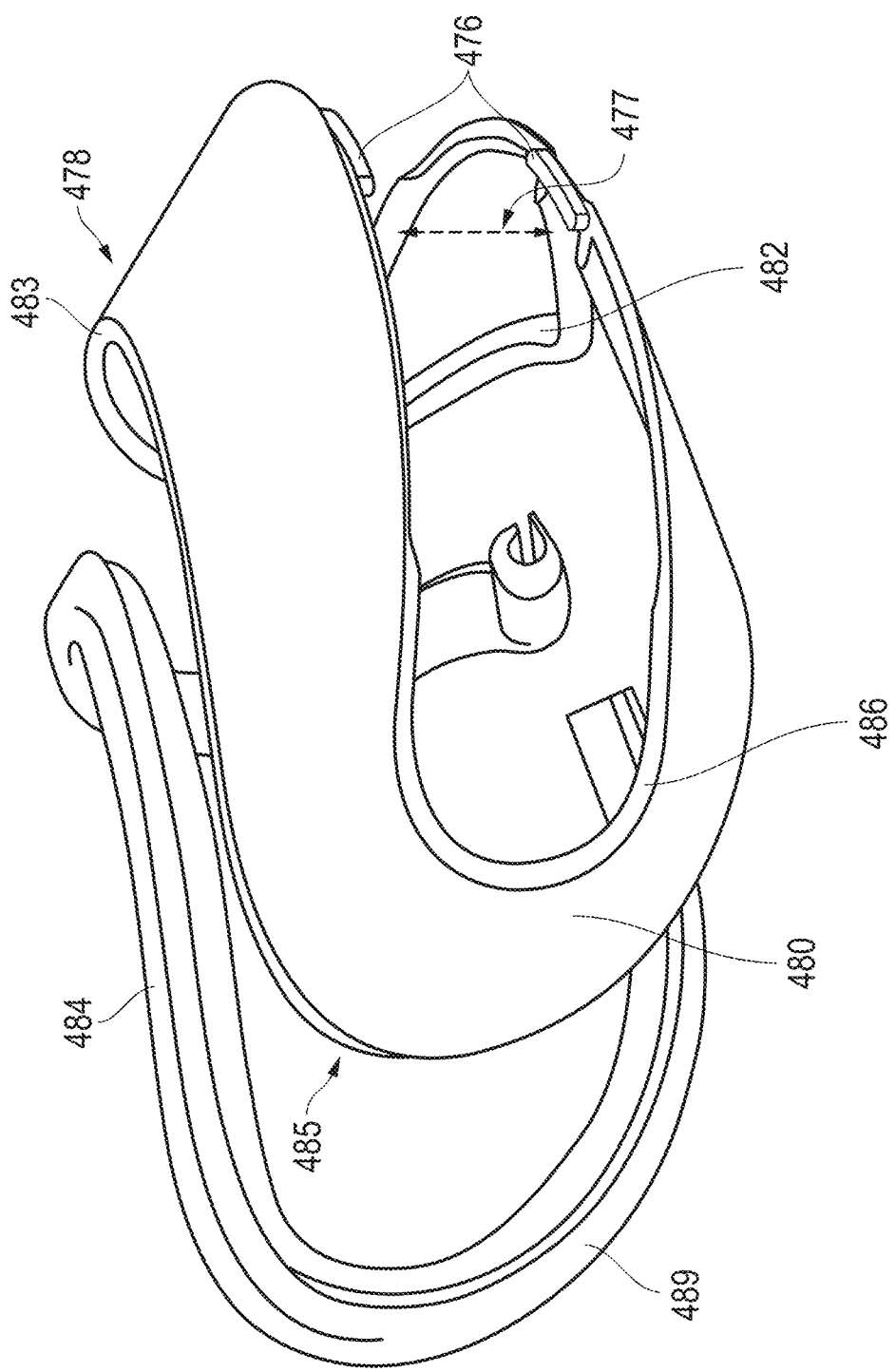
FIG. 4 is a graphic diagram perspective view of an HMD hood of an XR HMD device according to an embodiment of the present disclosure.

FIG. 4 is a graphical diagram perspective view of an HMD hood 478 of an HMD device according to an embodiment of the present disclosure. As described herein, the HMD hood 478 may be a removable part of the HMD device. The HMD hood 478 in FIG. 4 shows a front aperture 477 with a first edge or distal edge from the user around the front aperture 477 having one or more hood teeth 476 and a shroud seal 486. The front aperture 477 is to receive the HMD device into the HMD hood 478. FIG. 4 shows the HMD hood 478 with the face mask 484 removed from the face mask 484 frame bead or frame lip 483 on a second edge or proximal edge 485 around the back aperture of the shroud frame 482 that is closer to and faces the user while wearing the HMD device. FIG. 4 shows the face mask 484 having a bead channel 489 in an embodiment. The bead channel 489 may receive the face mask frame bead or frame lip 483 of the shroud frame 482 in order to install the face mask 484 onto the HMD hood 478. As described herein, the face mask 484 installed on the second edge or distal edge 485 is around the back aperture of the HMD hood 478 and is used to abut a user's face when the HMD device is worn. The face mask 484 may be made of a pliable material such as a foam or silicone in order to soften the interface between the HMD device and the user's face making the wearing of the HMD device more comfortable to the user.

The HMD hood 478 may include a fabric shroud 480 laid over a shroud frame 482 and operatively coupled to the HMD shield via the interaction between one or more shield slots (not shown) and one or more hood teeth 476 formed at a distal first edge around the front aperture 477 of the shroud frame 482. The shroud frame 482 may be a lightweight piece of plastic that is skeletonized and includes one or more supporting members for the fabric shroud 480 to be draped over the shroud frame 482. With this skeletonized structure of the shroud frame 482, the amount of materials used to form the HMD hood 478 thereby reducing the weight of the HMD hood 478 and, accordingly, the overall weight of the HMD device. The fabric shroud 480 may be made of any material that prevents light from entering through the HMD hood 478 and into the user-viewing area within the HMD device.

In an embodiment, the fabric shroud 480 includes three layers of fabric. A first fabric shroud layer may include directionally-oriented moisture wicking fibers. During operation of the HMD device, a user and the HMD video display (not shown) may generate an amount of heat within the HMD hood 478. Along with this heat, the user may perspire or fluids in the user's eyes may evaporate into the user-viewing area. This evaporation creates microscopic droplets of sweat and other fluids that are trapped within the user-viewable area. However, the first fabric shroud layer includes directionally-oriented moisture wicking fibers that traps these microscopic droplets of sweat and other fluids and wicking them out of and away from the user-viewing area. The directionally-orientated moisture wicking fibers may be arranged to wick the moisture to a less dense portion of the first fabric shroud layer that is away from the user-viewing area. This first fabric shroud layer may, therefore, prevent condensation from building up inside the HMD hood 478 or on the HMD video display, and prevents an uncomfortable physical environment for the user.

The fabric shroud 480 may further include, in an embodiment, a second layer and a third layer each used to prevent light from entering the HMD hood 478 and into the user-viewing area. The second layer may include fibers that are woven in a first direction while the third layer includes fibers woven in a second direction that is different from the first direction. In an embodiment, the direction of the woven fibers of the second layer and the third layer may be perpendicular to each other so that light may not pass through the HMD hood 478. The tightness of the weave of the second layer and third layer may be sufficient to allow the moisture wicked away from inside the HMD hood 478 by the first fabric shroud layer to pass through the second layer and third layer in those embodiments where the first layer is interior to the HMD hood 478 relative to the second and third layers. In another embodiment, the second or third layers of the fabric shroud 480 may be interior to the first layer of the fabric shroud 480.

The HMD hood 478 may further include one or more hood teeth 476 formed on the first or distal edge around the front aperture 477 of the shroud frame 482 of the HMD hood 478. FIG. 4 shows two hood teeth 476 formed at a top, distal first edge of the HMD hood 478 with the other hood tooth 476 formed at a bottom, distal first edge of the shroud frame 482. With a first hood tooth 476 on a top, distal edge of the shroud frame 482 and a second or additional hood teeth 476 formed at a distal, bottom first edge of the shroud frame 482, the shroud frame 482 may be elastically bent so that the hood teeth 476 are separated further from each other to expand the front aperture 477 to a wider opening than what is shown in FIG. 4 by the dashed, double-ended arrow. This separation of the hood teeth 476 away from each other may facilitate the user in installing or removing the HMD hood 478 with or from the HMD shield via the front aperture 477 respectively by seating or unseating the hood teeth 476 in the shield slots in the HMD shield as described herein. In other embodiments, a snap fit or interference fit may be used between the hood teeth 476 and shield slot.

During use, the users operating the HMD device may perspire or otherwise create a situation where bacteria or viruses can be spread. In order to mitigate this transmission of bacteria or viruses, each user of the HMD device may be assigned an HMD hood 478 with face mask 484 that the user may use with the HMD device 454. In an embodiment, the user may be allowed to purchase additional HMD hoods 478 for this purpose. In an embodiment, the HMD device 454 may be shipped to the user with a plurality of HMD hoods 478 as described herein. With the easy removal and coupling of the HMD hood 478 to the HMD shield as described herein, the user is allowed to easily remove their assigned HMD hood 478 after using the HMD device allowing the next user to couple their assigned HMD hood 478 to the HMD shield of the HMD device. Further, removal of the HMD hood 478 is simplified for cleaning or replacement.

In an embodiment, the shroud frame 482 may further include a shroud seal 486 formed along the first edge surface of the shroud frame 482 that abuts portions of the HMD shield of the HMD device. The shroud seal 486 may be a portion of the shroud frame 482 that conforms to a surface of the HMD shield when the HMD hood 478 is installed. In an embodiment, the HMD shield includes a shield groove (not shown) that interfaces with the shroud seal 486 which may be formed on a first, distal edge of the shroud frame 482 of the HMD hood 478 around the front aperture that interfaces with the HMD shield. This interfacing between the shroud seal such as an edge lip and shield groove prevents light from entering the user-viewing area within the HMD hood 478 thereby making the HMD hood 478 lightproof.

Figure 5:
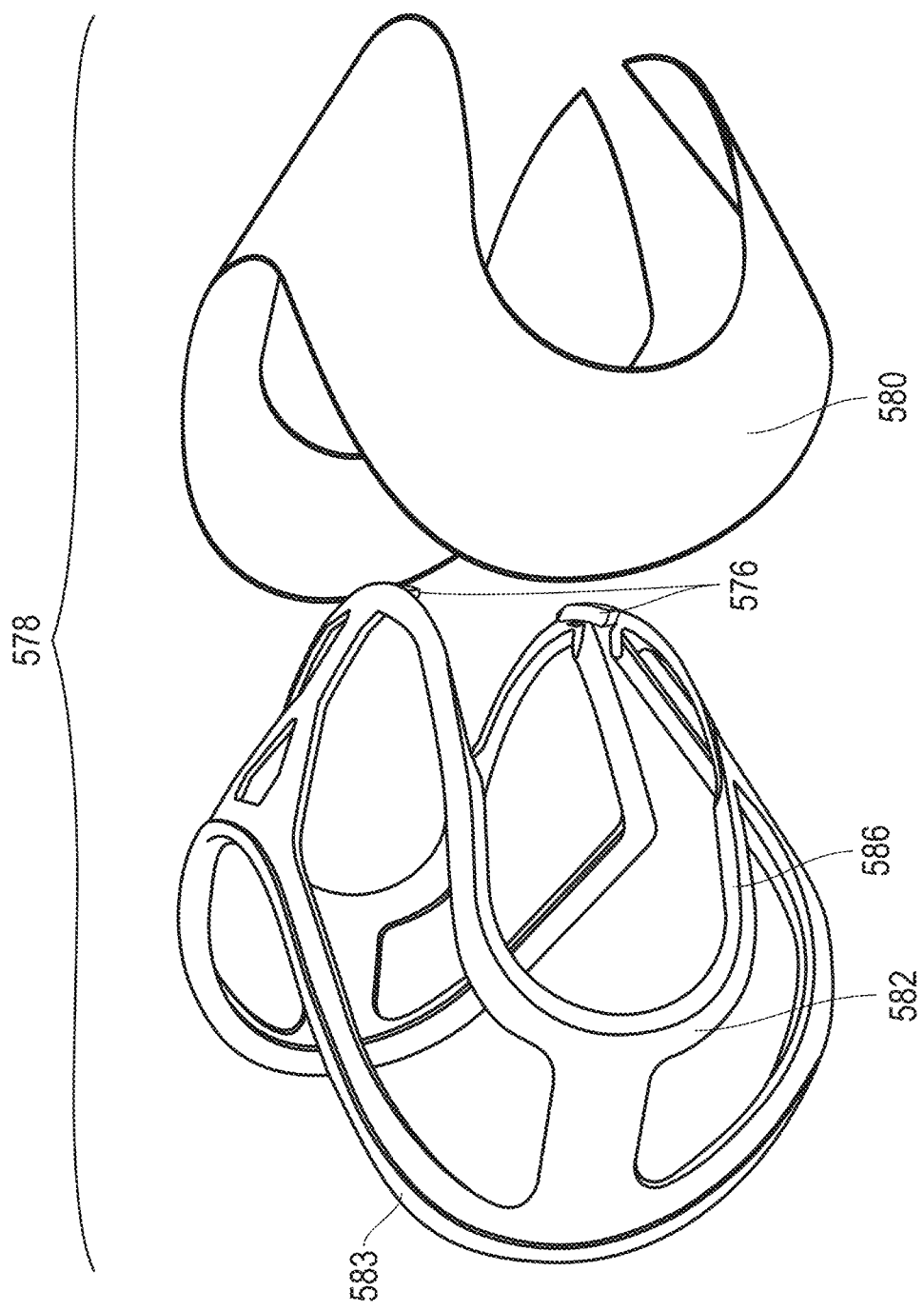
FIG. 5 is a graphic diagram exploded, perspective view of an HMD hood of an XR HMD device according to another embodiment of the present disclosure

FIG. 5 is a graphic diagram exploded, perspective view of an HMD hood 578 of an XR HMD device according to another embodiment of the present disclosure. FIG. 5 shows the HMD hood 578 without the face mask attached to the frame mask frame bead 583. FIG. 5 also shows the face mask frame bead 583 of the shroud frame 582 used to install the face mask onto the HMD hood 578.

The HMD hood 578 may include the fabric shroud 580 laid over a shroud frame 582. In an embodiment, the fabric shroud 580 may be secured to the shroud frame 582 via any clip, adhesive, screw, or other fastening device. In an embodiment, the fabric shroud 580 may be ultrasonically or heat welded to the shroud frame 582 at edge boundaries of the shroud frame 582. In an embodiment, the fabric shroud 580 includes three layers of fabric. A first fabric shroud layer may include directionally-oriented moisture wicking fibers. During operation of the HMD device, a user and the HMD video display (not shown) may generate an amount of heat within the HMD hood 578. Along with this heat, the user may perspire or fluids in the user's eyes may evaporate into the user-viewing area. This evaporation creates microscopic droplets of sweat and other fluids that are trapped within the user-viewable area. However, the first fabric shroud layer includes directionally-oriented moisture wicking fibers that traps these microscopic droplets of sweat and other fluids and wicking them out of and away from the user-viewing area. The directionally-orientated moisture wicking fibers may be arranged to wick the moisture to a less dense portion of the first fabric shroud layer that is away from the user-viewing area. This first fabric shroud layer may, therefore, prevent condensation from building up inside the HMD hood 578 and on the HMD video display, and prevent an uncomfortable physical environment for the user.

The fabric shroud 580 may further include, in an embodiment, a second layer and a third layer each used to prevent light from entering the HMD hood 578 and into the user-viewing area. The second layer may include fibers that are woven in a first direction while the third layer includes fibers woven in a second direction that is different from the first direction. In an embodiment, the direction of the woven fibers of the second layer and the third layer may be perpendicular to each other so that light may not pass through the HMD hood 578. The tightness of the weave of the second layer and third layer may be sufficient to allow the moisture wicked away from inside the HMD hood 578 by the first fabric shroud layer to pass through the second layer and third layer in those embodiments where the first layer is interior to the HMD hood 578 relative to the second and third layers. In another embodiment, the second or third layers of the fabric shroud 580 may be interior to the first layer of the fabric shroud 580.

The HMD hood 578 may further include one or more hood teeth 576 formed on the shroud frame 582 of the HMD hood 578. FIG. 5 shows two hood teeth 576 similar to those shown in FIG. 4. With a first hood tooth 576 on a top, distal edge of the shroud frame 582 and a second or additional hood teeth 576 formed at a distal, bottom edge of the shroud frame 582, the shroud frame 582 may be elastically bent so that the hood teeth 576 are separated further from each other. This separation of the hood teeth 576 away from each other may facilitate the user in installing or removing the HMD hood 578 with or from the HMD shield respectively to seat or unseat the hood teeth 576 in one or more shield slots (not shown) as described herein.

In an embodiment, the shroud frame 582 may further include a shroud seal 586 which may be an edge lip formed along a distal edge surface of the shroud frame 582 that abuts portions of the HMD shield of the HMD device. The shroud seal 586 may be a portion of the shroud frame 582 that conforms to a surface of the HMD shield when the HMD hood 578 is installed. In an embodiment, the HMD shield includes a shield groove (not shown) that interfaces with the shroud seal 586 such as an edge lip formed on the shroud frame 582 of the HMD hood 578. This interfacing between the shroud seal and shield groove prevents light from entering the user-viewing area within the HMD hood 578 thereby making the HMD hood 578 lightproof.

Figure 6:
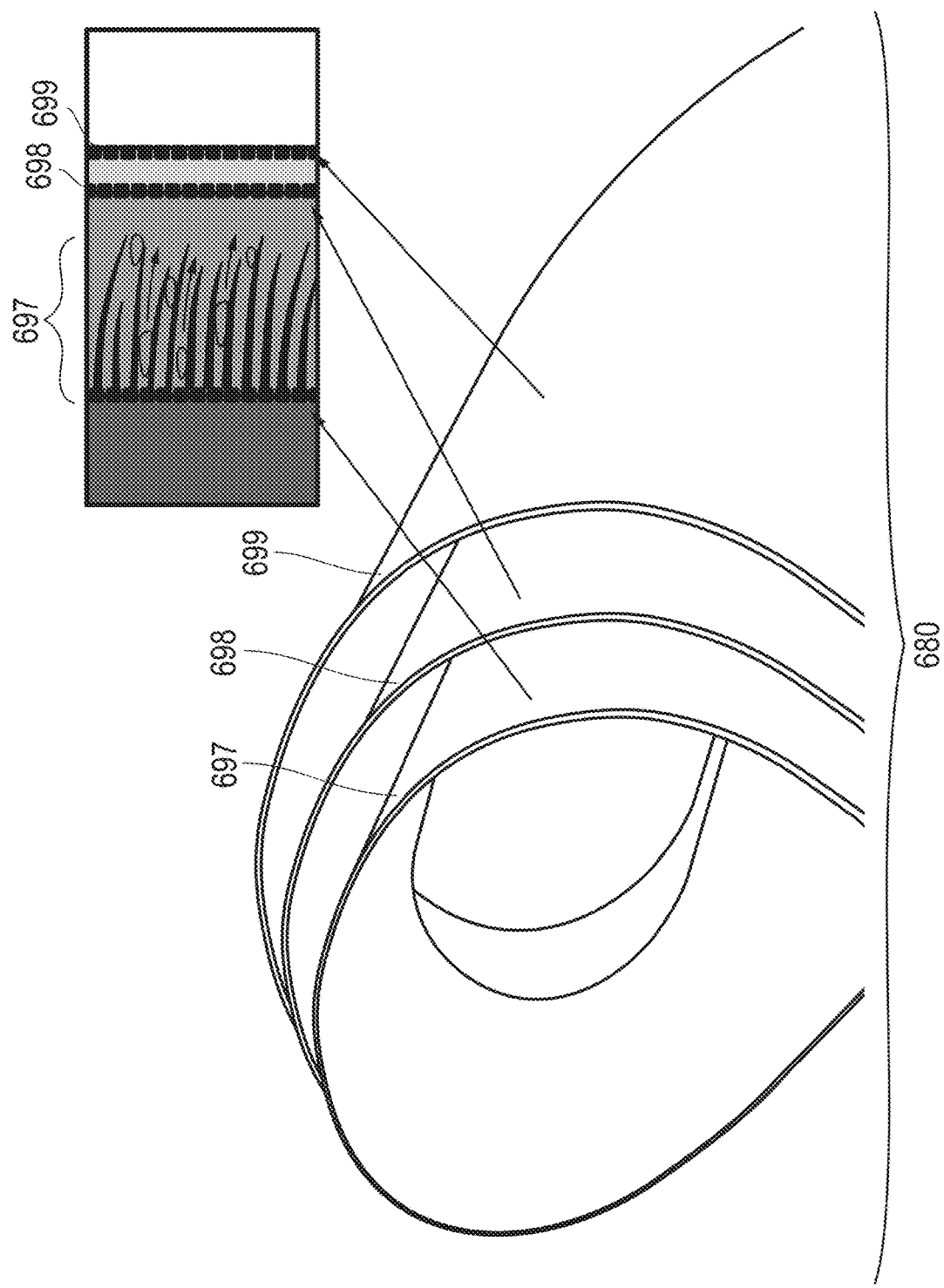
FIG. 6 is a graphic diagram perspective view of layers of a fabric shroud of an HMD hood according to another embodiment of the present disclosure.

FIG. 6 is graphic image perspective view of layers of a fabric shroud 680 of an HMD hood according to another embodiment of the present disclosure. FIG. 6 shows these layers separated from each other as well as a window showing a spatial relationship of these layers relative to each other. As described herein, the fabric shroud 680 includes three layers of fabric. A first shroud layer 697 may include directionally-oriented moisture wicking fibers. During operation of the HMD device, a user and the HMD video display may generate an amount of heat within the HMD hood 678. Along with this heat, the user may perspire or fluids in the user's eyes may evaporate into the user-viewing area. This evaporation creates microscopic droplets of sweat and other fluids that are trapped within the user-viewable area. However, the first shroud layer 697 includes directionally-oriented moisture wicking fibers that traps these microscopic droplets of sweat and other fluids and wicking them out of and away from the user-viewing area. In the window presented in FIG. 6, the user-viewing area internal to the HMD device is left of the first shroud layer 697 with these moisture wicking fibers directed away from the user-viewing area using, for example, capillary forces. The directionally-orientated moisture wicking fibers may be arranged to wick the moisture to a less dense portion of the first fabric shroud layer that is away from the user-viewing area. This first shroud layer 697 may, therefore, prevent or reduce condensation from building up inside the HMD hood, prevent fogging the HMD video display, and prevent an uncomfortable physical environment for the user.

The fabric shroud 680 may further include, in an embodiment, a second shroud layer 698 and a third shroud layer 699 each used to prevent light from entering the HMD hood and into the user-viewing area. The second shroud layer 698 may include fibers that are woven in a first direction while the third shroud layer 699 includes fibers woven in a second direction that is different from the first direction. In an embodiment, the direction of the woven fibers of the second shroud layer 698 and the third shroud layer 699 may be perpendicular to each other so that light may not pass through the HMD hood via the fabric shroud 680. The tightness of the weave of the second shroud layer 698 and third shroud layer 699 may be sufficient to allow the moisture wicked away from inside the fabric shroud 680 of the HMD hood by the first shroud layer 697 to pass through the second shroud layer 698 and third shroud layer 699 in those embodiments where the first shroud layer 697 is interior to the fabric shroud 680 relative to the second shroud layer 698 and third shroud layer 699. In another embodiment, the second shroud layer 698 or third shroud layer 699 of the fabric shroud 680 may be interior to the first layer of the fabric shroud 680.

Figure 7:
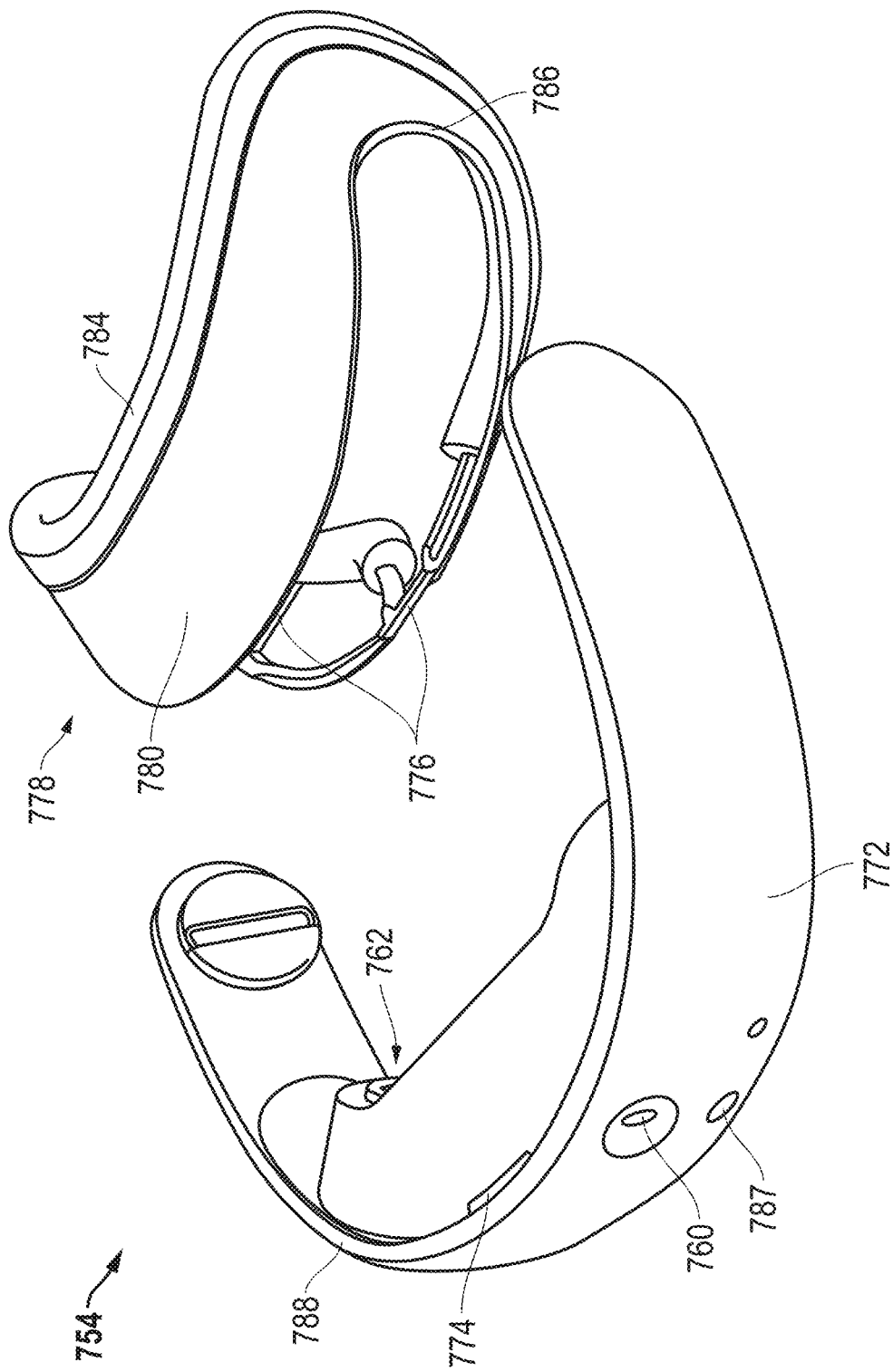
FIG. 7 is a graphic diagram perspective view of an HMD hood and an HMD shield of an HMD device according to an embodiment of the present disclosure.

FIG. 7 is a graphic diagram perspective view of an HMD hood 778 and an HMD shield 772 of an HMD device 754 according to an embodiment of the present disclosure. FIG.

7 shows a relative position of the HMD hood 778 to the HMD shield 772 when a user is installing the HMD hood 778 onto the HMD shield 772. Again, because the area between the user's eyes and the HMD video display 762 needs to be dark, the HMD hood 778 may prevent light from entering this area. In an embodiment, the HMD hood 778 may be lightproof so that the user may view the images and videos presented to the user at the HMD video display 762. In an embodiment, the HMD hood 778 may include a shroud frame (not shown) that maintains a shape of a fabric shroud 780 around the user's eyes and away from the HMD video display 762. In an embodiment, the shroud frame of the HMD hood 778 may include a face mask 784 used to abut a user's face when the HMD device 754 is worn and shown installed in FIG. 7. The face mask 784 may be made of a pliable material such as a foam or silicone in order to soften the interface between the HMD device 754 and the user's face making the wearing of the HMD device 754 more comfortable to the user.

The HMD device 754 may include an HMD shield 772 in an embodiment. The HMD shield 772 may act as part of the housing on to which other components of the HMD device 754 may be secured or into which some of the hardware of the HMD device 754 may be placed. For example, the HMD device 754 may include a camera/pass-through camera 760 used to provide data to a processing resource describing the location of the HMD device 754 within a physical environment. Additionally, the camera/pass-through camera 760 may provide images to the user via the HMD video display 762 of the physical environment around the user. The camera/pass-through camera 760 may be formed into a front portion of the HMD shield 772 and protected from the rigid housing of the HMD shield 772 from damage.

The HMD shield 772 may also house an IR detector/IR emitter 787. In an embodiment, the IR detector/IR emitter 787 or visible light versions of the same, for example, within either on the HMD device 754 (e.g., inward-out location detection) or located within the physical environment (e.g., outward-in location detection), may be used to triangulate or multilaterate the location of the HMD device 754 within the physical environment. In the example embodiment shown in FIG. 7, the IR detector/IR emitter 787 may also be placed within the housing of the HMD shield 792 to protect the IR detector/IR emitter 787 from damage.

The HMD hood 778 may include a fabric shroud 780 laid over a shroud frame and operatively coupled to the HMD shield 772 via and interaction between one or more shield slots 774 and one or more hood teeth 776 formed at a distal edge of the shroud frame. The shroud frame may be a lightweight piece of plastic that is skeletonized and includes one or more supporting members for the fabric shroud 780 to be draped over the shroud frame 782. As shown in FIG. 7, the shroud frame may include a distal edge that abuts the HMD shield 772 and a proximal edge that interfaces with a face mask 784 used to abut a user's face. The structure of the shroud frame 782 reduces the amount of materials used to form the HMD hood 778 thereby reducing the weight of the HMD hood 778 and, accordingly, the overall weight of the HMD device 754. The fabric shroud 780 may be made of any material that prevents light from entering through the HMD hood 778 and into the user-viewing area within the HMD device 754 such as that area between the user's eyes and the HMD video display 762 when the HMD device 754 is being worn.

In an embodiment, the fabric shroud 780 includes three layers of fabric. A first fabric shroud layer may include directionally-oriented moisture wicking fibers. The first fabric shroud layer includes directionally-oriented moisture wicking fibers that traps microscopic droplets of sweat and other fluids and wicking them out of and away from the user-viewing area. The directionally-orientated moisture wicking fibers may be arranged to wick the moisture to a less dense portion of the first fabric shroud layer that is away from the user-viewing area. This first fabric shroud layer may, therefore, prevent condensation from building up inside the HMD hood 778, prevent fogging of the HMD video display 762, and prevent an uncomfortable physical environment for the user. The fabric shroud 780 may further include, in an embodiment, a second layer and a third layer each used to prevent light from entering the HMD hood 778 and into the user-viewing area. The second layer may include fibers that are woven in a first direction while the third layer includes fibers woven in a second direction that is different from the first direction. In an embodiment, the direction of the woven fibers of the second layer and the third layer may be perpendicular to each other so that light may not pass through the HMD hood 778. The tightness of the weave of the second layer and third layer may be sufficient to allow the moisture wicked away from inside the HMD hood 778 by the first fabric shroud layer to pass through the second layer and third layer.

The HMD hood 778 may further include one or more hood teeth 776 formed on the shroud frame 782 of the HMD hood 778. FIG. 7 shows a hood tooth 776 formed at a top, distal first edge around a front aperture of the HMD hood 778 while another hood tooth 776 is formed at a bottom, distal front edge of the shroud frame 782 at the bottom of the front aperture of the HMD hood 778. With a first hood tooth 776 on a top, distal edge of the shroud frame 782 and the hood tooth 776 formed at a distal, bottom first edge of the shroud frame 782, the shroud frame 782 may be elastically bent so that the hood teeth 776 are separated further from each other when the HMD device is inserted into the front aperture of the HMD hood 778. This separation of the hood teeth 776 away from each other may facilitate the user in installing or removing the HMD hood 778 with or from the HMD shield 772, respectively.

In an embodiment, the HMD deice 354 is inserted into the front aperture of the HMD hood 778 by distending teeth 776 away from one another. Then, the hood teeth 776 may be placed within a shield slot 774 formed in an HMD shield 772 portion of the HMD device 754 while installed or being installed by the user. When being installed and when the user or the sliding of the HMD device 754 into the front aperture to align the teeth 776 with the shield slot 774 releases the force used to separate the hood teeth 776 from each other, the hood teeth 776 are allowed to be seated into their respective shield slots 774 thereby securing the HMD hood 778 to the HMD shield 772 and the other parts of the HMD device 754. In some embodiments, a snap fit or interference fit secures the hood teeth 776 in the shield slot or slots 774. This allows a user to easily swap out a first HMD hood 778 for a second HMD hood 778 for cleaning or replacement. For example, the HMD device 754 may be provided with a plurality of different sized or extra HMD hoods 778. The different sizes of HMD hoods 778 may allow a user to select, from among the plurality of HMD hoods 778, a single HMD hood 778 that is sized for the user's face the best. Additionally, the user may select a specific HMD hood 778 to be used by the user throughout the lifetime of the HMD device 754. This may allow multiple users to operate the HMD device 754 using their own HMD hood 778. During use, the users operating the HMD device 754 may perspire or otherwise create a situation where bacteria or viruses can be spread. In order to mitigate this transmission of bacteria or viruses, each user of the HMD device 754 may be assigned an HMD hood 778 that the user may use with the HMD device 754. In an embodiment, the user may be allowed to purchase additional HMD hoods 778 for this purpose. In an embodiment, the HMD device 754 may be shipped to the user with a plurality of HMD hoods 778 as described herein. With the easy removal and coupling of the HMD hood 778 to the HMD shield 772 as described herein, the user is allowed to easily remove their assigned HMD hood 778 after using the HMD device 754 allowing the next user to couple their assigned HMD hood 778 to the HMD shield 772 of the HMD device 754.

In an embodiment, the shroud frame 782 may further include a shroud seal 786 formed along a distal edge surface of the shroud frame 782 that abuts portions of the HMD shield 772 of the HMD device 754. The shroud seal may be a portion or a lip along a front edge of the shroud frame 782 that conforms to a surface of the HMD shield 772 when the HMD hood 778 is installed. In an embodiment, the HMD shield 772 includes a shield groove 788 that interfaces with the shroud seal 786, such as a lip, formed on the front edge of the shroud frame 782 around the front aperture of the HMD hood 778. This interfacing between the shroud seal 786 and shield groove 788 prevents light from entering the user-viewing area within the HMD hood 778 thereby making the HMD hood 778 lightproof.

As described herein, the HMD hood 778 may include a face mask 784 on a second edge of the HMD hood 778 around a back aperture, the face mask 784 is used to abut a user's face when the HMD device 754 is worn. The face mask 784 may be made of a pliable material such as a foam or silicone in order to soften the interface between the HMD device 754 and the user's face making the wearing of the HMD device 754 more comfortable to the user. In an embodiment, the shroud frame 782 may include a frame bead or face mask lip formed along a proximal, second edge around the back aperture of the shroud frame 782 proximate to a user's face when the HMD device is being worn. The frame bead or face mask lip may interface with a bead channel formed along a length of the face mask 784 that allows the face mask 784 to be wrapped around the frame bead securing the face mask 784 to the HMD hood 778.

Figure 8:
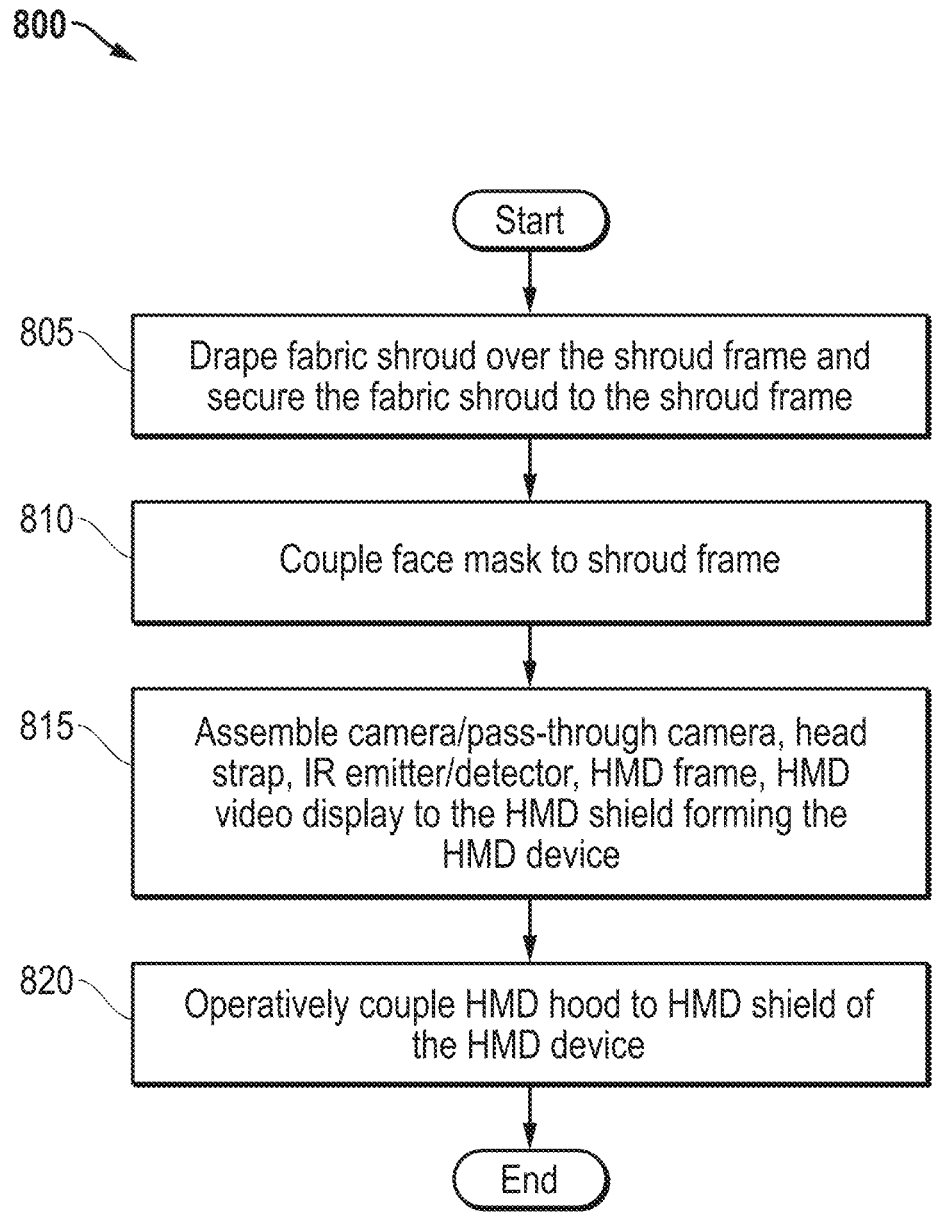
FIG. 8 is a flow diagram illustrating a method of manufacturing an HMD device with an HMD hood according to an embodiment of the present disclosure.

FIG. 8 is a flow diagram illustrating a method of manufacturing an HMD device with an HMD hood according to an embodiment of the present disclosure. The method 800 may include, at block 805, draping a fabric shroud over the shroud frame and securing the fabric shroud to the shroud frame. In an embodiment, the shroud frame may be made of lightweight and flexible plastic. In an embodiment, the formation of the shroud frame may be done by an injection molding process. The fabric shroud may be affixed to an outer surface of the shroud frame. In an embodiment, the fabric shroud may be affixed to an outer surface of the shroud frame using an ultrasonic welding process. Other processes and fastening devices may be used to secure the fabric shroud to the shroud frame. In an embodiment, the fabric shroud includes two or more layers of fabric. In a particular embodiment, the fabric shroud includes three layers of fabric. A first fabric shroud layer may include directionally-oriented moisture wicking fibers. These directionally-oriented moisture wicking fibers traps microscopic droplets of sweat and other fluids and wicks them out of and away from the user-viewing area. A second layer and a third layer may also be included with the first layer with each of the first layer and second layer used to prevent light from entering the HMD hood and into the user-viewing area. The second layer may include fibers that are woven in a first direction while the third layer includes fibers woven in a second direction that is different from the first direction. These opposite fiber weave directions may assist in preventing outside light from leaking into the HMD hood.

At block 810, the method 800 may proceed with coupling the face mask of the HMD hood to the shroud frame. The face mask may be a structure made of a pliable material such as a foam or silicone in order to soften the interface between the HMD device and the user's face making the wearing of the HMD device more comfortable to the user. The face mask comprises a bead channel formed along a length of the face mask that allows the face mask to be wrapped around a frame bead or edge lip formed on the shroud frame on a side facing the user when the HMD device is being worn. This frame bead and bead channel are operatively coupled to secure the face mask foam or silicone structure to the shroud frame edge. The face mask is formed and shaped to fit around the plastic edge of the shroud frame that faces the user putting on the HMD device.

At block 815, the method 800 includes the construction of the HMD device worn by the user. Proceeding to block 815, a camera/pass-through camera, head strap, IR emitter/detector, and HMD video display assembled into the HMD shield thereby forming the HMD shield of the HMD device. In an embodiment, of any of an HMD processor, HMD wireless devices, or other resources may be assembled in the HMD shield. In other embodiments, the IR emitter/detector, the camera/pass-through camera, and HMD video display may be operatively coupled to, for example, a printed circuit board (PCB) within the HMD shield so that these devices may be operatively coupled, via the PCB circuitry and an HMD connection wire as described in connection with FIG. 2 to other processing, power/battery, wireless radio and data storage resources at, for example, a compute stick or off-site compute compartment in an embodiment.

The method 800 further includes, at block 820, operatively coupling the HMD hood to the HMD shield of the HMD device. As described herein, the HMD hood may further include one or more hood teeth formed on the shroud frame during the injection molding process, for example. In one embodiment, a first hood tooth may be formed on a distal top edge of the shroud frame. In another embodiment, a second hood tooth may be formed on a distal bottom edge of the shroud frame. An edge lip or interference seal surface may be formed around the distal edge of the shroud frame that interfaces with the HMD shield. With the first hood tooth on a top distal edge of the shroud frame and the second hood tooth at a distal bottom edge of the shroud frame, the shroud frame may be elastically bent so that the hood teeth are separated further from each other. In an embodiment, the hood teeth may be placed within a shield slot formed in an HMD shield portion of the HMD device. The user may then release the shroud frame allowing the hood teeth to seat into their respective shield slots thereby securing the HMD hood to the HMD shield and the other parts of the HMD device. In an example embodiment, a snap fit or interference fit may be used to secure the hood teeth in the shield slots. The edge lip or interference seal surface may interface with an edge or groove structure on the HMD shield to further prevent light from leaking in. This allows a user to easily swap out a first HMD hood for a second HMD hood. Once assembled, the method 600 may end.

The blocks of the flow diagrams of FIG. 8 or steps and aspects of the operation of the embodiments herein and discussed above need not be performed in any given or specified order. It is contemplated that additional blocks, steps, or functions may be added, some blocks, steps or functions may not be performed, blocks, steps, or functions may occur contemporaneously, and blocks, steps or functions from one flow diagram may be performed within another flow diagram.

Devices, modules, resources, or programs that are in communication with one another need not be in continuous communication with each other, unless expressly specified otherwise. In addition, devices, modules, resources, or programs that are in communication with one another can communicate directly or indirectly through one or more intermediaries.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims. In the claims, means-plus-function clauses are intended to cover the structures described herein as performing the recited function and not only structural equivalents, but also equivalent structures.

The above-disclosed subject matter is to be considered illustrative, and not restrictive, and the appended claims are intended to cover any and all such modifications, enhancements, and other embodiments that fall within the scope of the present invention. Thus, to the maximum extent allowed by law, the scope of the present invention is to be determined by the broadest permissible interpretation of the following claims and their equivalents, and shall not be restricted or limited by the foregoing detailed description.

What is claimed is:

1. An extended reality (XR) head mounted display (HMD) device comprising:
   a processor;
   a memory device;
   a power management unit;
   an HMD video display of the HMD device to present to a user an extended reality image of an environment; and
   an HMD housing fitted to be formed around a user's eyes, the HMD housing including an HMD shield having the HMD video display mounted therein;
   an HMD hood comprising a fabric shroud operatively coupled to a shroud frame and a face mask operatively coupled to the shroud frame to interface with a user's face, where the fabric shroud extends from the face mask on the shroud frame to a distal aperture of the shroud frame operatively coupled to the HMD shield; and
   the HMD hood operatively coupled to the HMD housing via fitting the HMD shield into the distal aperture, distal relative to the user's face, in the shroud frame of the HMD hood.

2. The XR HMD device of claim 1 further comprising:
   a hood tooth formed on a first edge around the distal aperture of the shroud frame into which the HMD housing is fitted, the hood tooth to operatively couple the HMD hood to the HMD shield via being seated in a shield slot formed in the HMD shield.

3. The XR HMD device of claim 1 further comprising:
   a shroud seal formed around the distal aperture along a first edge of the shroud frame to interface with a shield groove formed on the HMD shield, the shroud seal to make an interior of the HMD hood lightproof when installed on the HMD housing.

4. The XR HMD device of claim 1 further comprising:
   the fabric shroud including:
       a first layer including directionally-oriented moisture wicking fibers;
       a second layer including fibers woven in a first direction; and
       a third layer including fibers woven in a second direction different from the first direction.

5. The XR HMD device of claim 1 further comprising:
   the shroud frame being made of a pliable material, the shroud frame including a set of hood teeth that engage with a plurality of shield slots in the HMD shield by elastically bending the shroud frame over the HMD shield and into the plurality of shield slots when the HMD shield is inserted into the distal aperture in the shroud frame of the HMD hood.

6. The XR HMD device of claim 1, wherein the face mask is made of silicone.

7. The XR HMD device of claim 1, wherein the fabric shroud is welded onto the shroud frame along a fabric shroud perimeter formed on the shroud frame.

8. The XR HMD device of claim 1, wherein the shroud frame is made of a pliable plastic that bends to conform to a user's face when the HMD device is worn.

9. The XR HMD device of claim 1 further comprising:
   a frame bead formed along a proximal edge of the shroud frame facing the user, the frame bead to interface with a bead channel formed in the face mask to mount the face mask on the shroud frame.

10. A head mounted display (HMD) hood operatively coupled to an extended reality (XR) HMD device having an HMD shield comprising:
    a shroud frame operatively coupled to the HMD shield, having a front distal aperture, and including a hood tooth formed on a first edge of the front, distal aperture of the shroud frame to operatively couple with a shield slot formed into the HMD shield of the HMD device;
    a fabric shroud operatively coupled across the shroud frame from a proximal aperture of the shroud frame to the front, distal aps of the shroud frame, the fabric shroud including a plurality of fabric layers to wick moisture and block light from an HMD video display formed in the HMD shield of the HMD device that is operative coupled within the front, distal aperture of the shroud frame of the HMD hood; and
    a face mask operatively coupled to the shroud frame.

11. The HMD hood of claim 10 further comprising:
    a shroud seal formed on the first edge of the shroud frame along the front, distal aperture to operatively couple with a shield groove formed on the HMD shield, where the shroud seal prevent light leaking into an interior of the HMD hood.

12. The HMD hood of claim 10 further comprising:
    the shroud frame being made of a pliable material, wherein the hood tooth is operatively coupled with a shield slot formed into the HMD shield of the HMD device by elastically bending the shroud frame over the HMD shield and into the shield slot.

13. The HMD hood of claim 10, wherein the fabric shroud is welded or adhered onto the shroud frame along a fabric shroud perimeter formed on the shroud frame.

14. The HMD hood of claim 10 further comprising:
a frame bead formed along a second edge of the shroud frame around a proximal aperture facing a user, the frame bead to interface with a bead channel formed in the face mask.

15. The HMD hood of claim 10 further comprising:
the plurality of fabric layers including:
- a first layer including directionally-oriented moisture wicking fibers;
- a second layer including fibers woven in a first direction; and
- a third layer including fibers woven in a second direction different from the first direction.

16. An extended reality (XR) head mounted display (HMD) device comprising:
a processor;
a memory device;
a power management unit;
an HMD device to present to a user an extended reality image of an environment via an HMD video display mounted within an HMD shield;
the HMD shield fitted into an HMD hood to be formed around a user's eyes;
the HMD hood including:
- a shroud frame including a hood tooth formed on a first edge around a front, distal aperture of the shroud frame to couple with a shield slot formed into the HMD shield of the HMD device;
- a fabric shroud operatively coupled across the shroud frame from a proximal aperture of the shroud frame to a front, distal aperture of the shroud frame to receive the HMD shield, the fabric shroud including a plurality of fabric layers to wick moisture and block light from the HMD video display in the HMD shield of the HMD device installed within the HMD hood; and
- a face mask operatively coupled to the shroud frame; and
an adjustable strap mounted to the HMD shield to fit around a user's head.

17. The XR HMD device of claim 16, further comprising:
the plurality of fabric layers including a first layer including directionally-oriented moisture wicking fibers.

18. The XR HMD device of claim 16, further comprising:
a shroud seal formed on the shroud frame to interface with a shield groove formed on the HMD shield, the shroud seal to prevent light from leaking into an interior of the HMD hood.

19. The XR HMD device of claim 16, further comprising:
the plurality of fabric layers including:
- a first layer including fibers woven in a first direction; and
- a second layer including fibers woven in a second direction different from the first direction.

20. The XR HMD device of claim 16, further comprising:
a frame bead formed along a second edge of the shroud frame around a proximal aperture of the shroud frame to face the user, the frame bead to interface with a bead channel formed in the face mask to operatively couple the face mask to the shroud frame.

* * * * *